US011116395B1

(12) United States Patent
Gur

(10) Patent No.: US 11,116,395 B1
(45) Date of Patent: Sep. 14, 2021

(54) COMPACT RETINAL SCANNING DEVICE FOR TRACKING MOVEMENT OF THE EYE'S PUPIL AND APPLICATIONS THEREOF

(71) Applicant: EYEJETS LTD., Kidron (IL)

(72) Inventor: Joshua Gur, Jerusalem (IL)

(73) Assignee: EyeJets Ltd., Kidron (IL)

( * ) Notice: Subject to any disclaimer, the term of this patent is extended or adjusted under 35 U.S.C. 154(b) by 0 days.

(21) Appl. No.: 17/289,194

(22) PCT Filed: Oct. 2, 2020

(86) PCT No.: PCT/IL2020/051074
§ 371 (c)(1),
(2) Date: Apr. 27, 2021

(87) PCT Pub. No.: WO2021/064734
PCT Pub. Date: Apr. 8, 2021

(30) Foreign Application Priority Data

Oct. 3, 2019 (IL) .......................................... 269809

(51) Int. Cl.
*A61B 3/113* (2006.01)
*A61B 3/10* (2006.01)
(Continued)

(52) U.S. Cl.
CPC ............ *A61B 3/113* (2013.01); *A61B 3/1025* (2013.01); *G02B 26/129* (2013.01);
(Continued)

(58) Field of Classification Search
CPC .............. G02B 26/129; G02B 27/0093; G02B 27/0172; G02B 2027/0138; A61B 3/113; A61B 3/1025
(Continued)

(56) References Cited

U.S. PATENT DOCUMENTS 6,027,216 A * 2/2000 Guyton ................... A61B 3/113
351/200
2003/0179344 A1* 9/2003 Velde ...................... A61F 9/008
351/200
(Continued)

OTHER PUBLICATIONS

Eye tracking for research. Tobiipro. Accessed at https://www.tobiipro.com/ on Apr. 12, 2021. 3 pages.
(Continued)

*Primary Examiner* — Mohammed A Hasan
(74) *Attorney, Agent, or Firm* — Smith Baluch LLP

(57) ABSTRACT

A tracking scanning laser optics device configured for mounting in hedger having at least one opening for positioning in front of an eye of a user includes a mounting unit, an invisible light source supported by the mounting unit for directing invisible light through pupil, and at least one visible light source supported by the mounting unit for directing visible light through the pupil for writing on the retina within a portion thereof scanned by 2-D scanning optics supported by the mounting unit. An imaging device supported by the mounting unit receives at least the invisible light reflected by the retina and stores an image thereof, and a calibration unit operative in conjunction with the 2-D scanning optics determines an origin in 2-D space for serving as a reference point for identifying a location of the portion within the retina.

39 Claims, 14 Drawing Sheets

(51) Int. Cl.
*G02B 27/00* (2006.01)
*G02B 26/12* (2006.01)
*G02B 27/01* (2006.01)

(52) U.S. Cl.
CPC ..... *G02B 27/0093* (2013.01); *G02B 27/0172* (2013.01); *G02B 2027/0138* (2013.01)

(58) Field of Classification Search
USPC .......................................................... 351/209
See application file for complete search history.

(56) References Cited

U.S. PATENT DOCUMENTS

| | | | |
|---|---|---|---|
| 2007/0091265 A1* | 4/2007 | Kardon | A61B 3/0058 351/206 |
| 2012/0105310 A1* | 5/2012 | Sverdrup | G02B 27/0172 345/8 |
| 2017/0188021 A1 | 6/2017 | Lo et al. | |
| 2018/0232575 A1* | 8/2018 | Strombom | H04N 7/18 |
| 2019/0222830 A1* | 7/2019 | Edwin | G06F 3/167 |

OTHER PUBLICATIONS

International Search Report and Written Opinion in International Application No. PCT/IL2020/051074 dated Mar. 25, 2021, 7 pages.

* cited by examiner

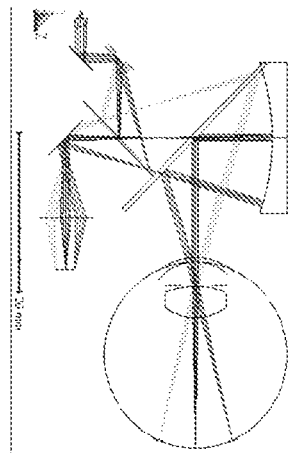 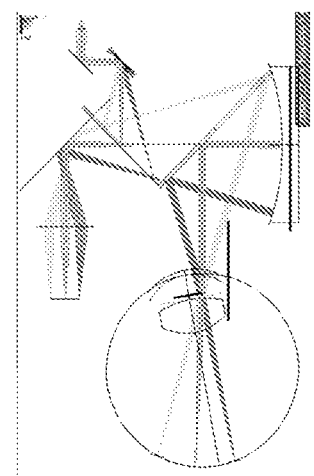 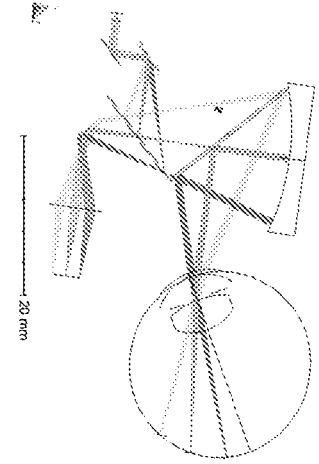
FIG. 3a　　　　FIG. 3b　　　　FIG. 3c
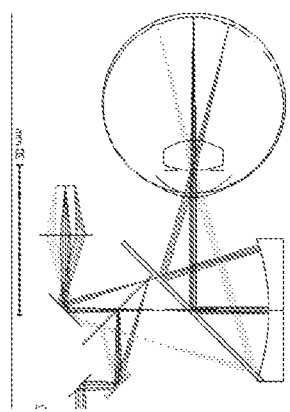
FIG. 4a
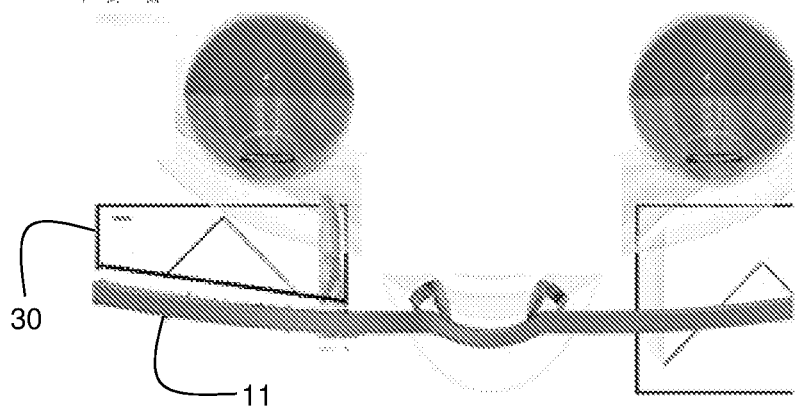
FIG. 4b

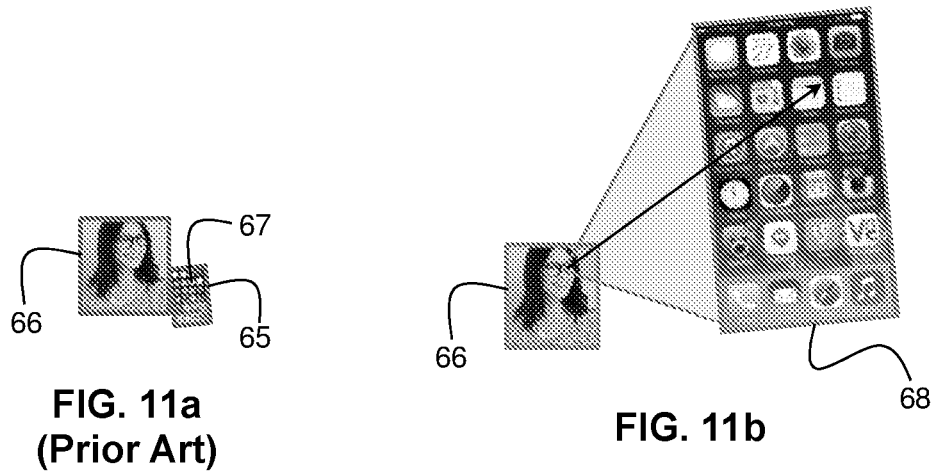
FIG. 11a
(Prior Art)
FIG. 11b
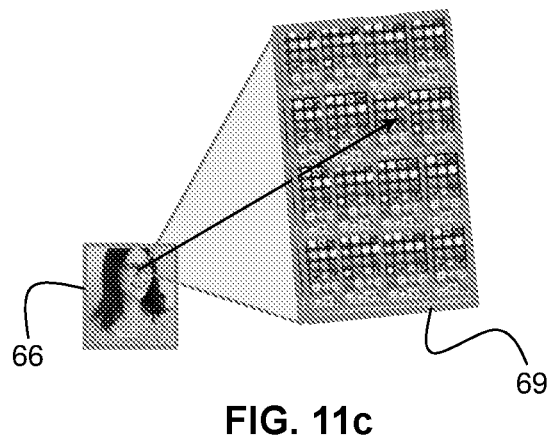
FIG. 11c
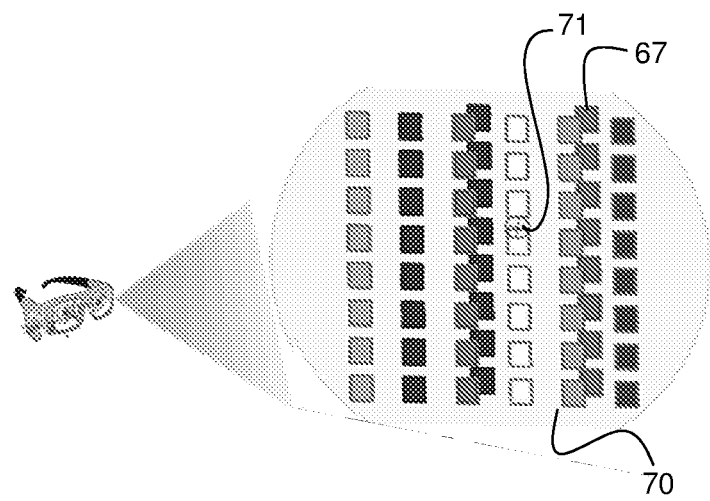
FIG. 11d

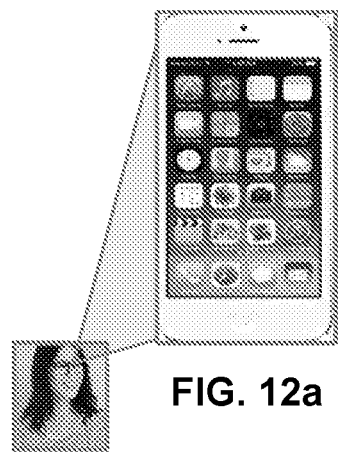
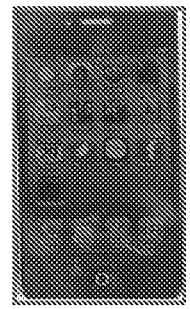
FIG. 12a
FIG. 12b (Prior Art)
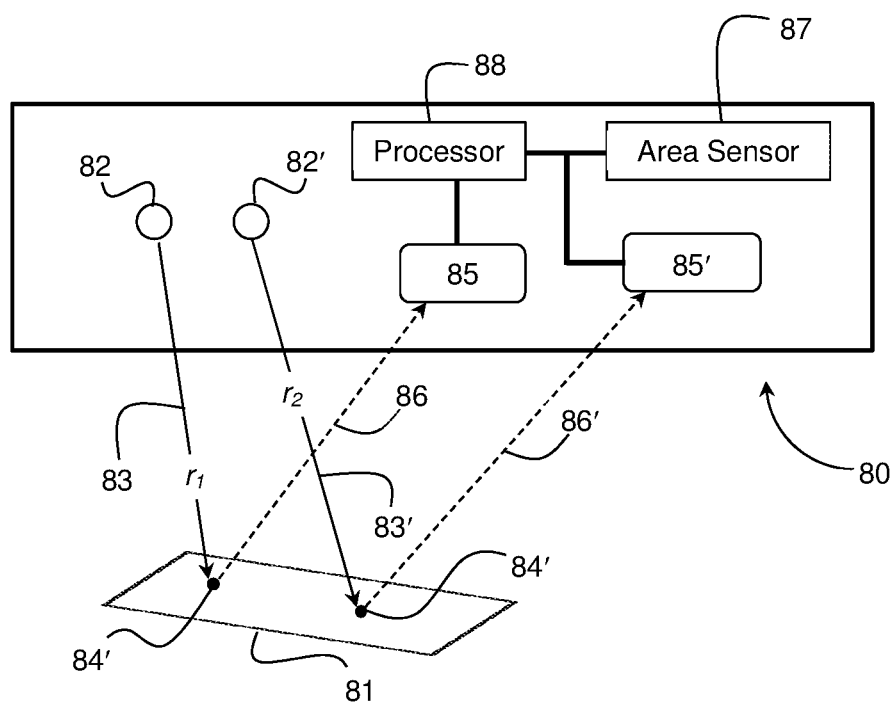
FIG. 13

COMPACT RETINAL SCANNING DEVICE FOR TRACKING MOVEMENT OF THE EYE'S PUPIL AND APPLICATIONS THEREOF

RELATED APPLICATIONS APPLICATION

This application is a national-stage application, under 35 U.S.C. 371, of PCT/IL2020/051074 filed Oct. 2, 2020, which claims priority from IL 269809 filed Oct. 3, 2019 the full contents of each of which including the Appendix of IL 269809 are incorporated herein by reference.

FIELD OF THE INVENTION

This invention relates in general to eye-tracking and in particular to tracking scanning laser ophthalmoscopy (TSLO) and applications thereof.

BACKGROUND OF THE INVENTION

Scanning laser ophthalmoscopy (SLO) utilizes horizontal and vertical scanning mirrors to scan a specific region of the retina and create raster images viewable on a television monitor. A known drawback of convention SLO is data corruption caused by eye movements, which is overcome using tracking scanning laser ophthalmoscopy (TSLO). TSLO systems direct light from a light source through the subject's pupil on to the retina, from which it is reflected back through the pupil, detected and analyzed using suitable software, which is configured to compute and compensate for eye movement. However, such systems are limited to small angular displacements of the eye, because if the subject's pupil rotates too far from its initial location, it will move out of alignment with the light source. TSLO systems are primarily intended for compensating for slight tremors during clinical measurements, which are conducted in a doctor's surgery with the subject's head clamped to prevent head movement and prior to which the pupil is dilated using eye drops. The dilation ensures that the pupil is sufficiently wide, that even allowing for minor tremors it will still remain in alignment with the light source.

However, while this assumption is valid in clinical settings it is not valid in outdoor settings where the subject's head is not clamped and his gaze is free to wander. Under these circumstances other forms of eye-tracking have been proposed. For example, it is known to mount eye-trackers on special-purpose headgear such as spectacles or helmets. One such system commercialized by Tobii AB (publ) of Stockholm, Sweden, https://www.tobiipro.com/ uses cameras to track eye motion for determining line-of-sight in applications such as identifying a consumer product in a consumer's line-of-sight and providing contextual marketing promotions.

The Tobii system tracks eye motion by reflecting light on to the cornea from which it is reflected and imaged allowing direction of gaze to be determined. However, there is no retinal scanning or facility to write on to the retina.

US 20170188021 discloses a retinal light scanning engine that writes light corresponding to an image on the retina of a viewer. A light source of the retinal light scanning engine forms a single point of light on the retina at any single, discrete moment in time. In one example, to form a complete image, the retinal light scanning engine uses a pattern to scan or write on the retina to provide light to millions of such points over one time segment corresponding to the image.

It is also known that the scanning laser ophthalmoscope (SLO) provides a high-quality television image of the retina using less than $\frac{1}{1000}$ of the light required for conventional indirect ophthalmoscopy. Retinal scanning provides an ideal vehicle for non-invasive monitoring of a patient's blood vessels, which can serve as a reliable biometric for glaucoma, diabetes, high blood pressure and other diseases. Currently, patients undergoing retinal scans using SLO are examined by an ophthalmologist often requiring repeated and periodic visits to the ophthalmologist's clinic. Eye drops are used to dilate the patient's pupils, a process which typically takes up to ten minutes during which time the patient waits in the waiting room and only after which the patient's eyes are examined During this examination, the patient's gaze is directed toward the ophthalmoscope and eye-tracking is not a concern. But it would clearly be of significant benefit to both the doctor and the patient, were the patient able to conduct the examination at home and transmit the results to the doctor for analysis, possibly under the doctor's direction, thus saving significant time for both. So far is known, no solution to this need has been proposed.

Establishing direction of gaze is also important in guidance systems, for which head-up displays are commonly used to allow a pilot or gunner to align a target with a reticle of the head-up display whereupon the guidance system is configured to direct a bomb or other projectile toward the target. However, such systems do not help infantry soldiers using rifles, whose sights must be geometrically aligned with the soldier's eyes and in the process obscure his vision and render him vulnerable to attack.

Another problem that is addressed by the invention relates to the poor outdoor visibility of mobile device display screens such as cellular telephones as well as their compact size, which makes it difficult to read large volume text. In a typical scenario, the screen image is enlarged by "zooming" using the thumb and forefinger, but this reduces the amount of text that is displayed at any given time. Likewise, smartphones often have settings that increase contrast automatically to compensate for high brightness ambient conditions. But in practice, they are of limited effectiveness, particularly in conditions of bright sunlight.

SUMMARY OF THE INVENTION

It is a principal object of the present invention to provide a highly compact eye tracking and scanning device that can be fitted or retro-fitted to regular eyeglasses.

In one application such a device allows a patient to perform retinal scanning at home and convey the results to his or her physician.

In another application such a device may be used to convey visual information electronically directly to the retina.

In another application such a device may be integrated with an automatic guidance system suitable for infantry soldiers that addresses defects of current target alignment.

These and other objectives are realized in accordance with a broad aspect of the invention by a tracking scanning laser optics device configured for mounting in headgear having at least one opening for positioning in front of an eye of a user, said tracking scanning laser optics device comprising:

a mounting unit integral with or configured for attachment to the headgear, an invisible light source supported by the mounting unit for directing invisible light through a pupil of the user for scanning and imaging a portion of the retina, at least one visible light source supported by the mounting unit for directing visible light through said pupil for writing on to the retina within said portion, 2-D scanning optics supported by the mounting unit for scanning said portion of the retina with the invisible and visible light, an imaging device supported by the mounting unit for receiving at least the invisible light reflected by said portion of the retina and storing an image thereof, and a calibration unit operative in conjunction with the 2-D scanning optics for determining an origin in 2-D space for serving as a reference point for identifying a location of said portion within the retina.

Preferably, the headgear is constituted by a pair of regular eyeglasses comprising a spectacle frame defining a pair of openings each for positioning in front of respective eyes of a user and having a pair of side-arms, the spectacle frame having a low profile with a maximum depth not exceeding 5 mm. In practice, this means that the device according to the invention can be mounted into a regular pair of spectacles of the kind used for correcting visual impairment, so that the scanner is indistinguishable from a pair of conventional reading spectacles.

The invisible light source is typically a low-energy infrared laser diode that directs light into a subject's pupil and is reflected back through the pupil by the retina and detected on a suitable image sensor. The visible light source is a visible laser diode that writes directly on to the retina. If color images are required, then a triad of laser diodes may be employed to provide R, G, B color sources.

The 2-D scanning optics includes a micro-electromechanical system that can be integrated into a suitable mounting unit that can be fixed to a regular spectacle frame. The spectacle frame can, of course, have corrective lenses if required by the user; but it may have plain glass or even be left empty.

The calibration unit typically includes a miniature camera that is used to image a defined object in space serving as a reference marker that defines an initial angle of sight. It should be borne in mind that by analogy the retina may be compared to a large image sensor having a vast number of pixels, of which only a relatively small number may be illuminated at any given time depending on the user's field of view. So if a user reads the display screen of a hand-held smartphone whose screen subtends at angle of 3° at a distance of 50 mm a much smaller area of the retina will be exposed to light than when the user observes an outdoor landscape at infinity with a large field of view.

Consequently, when the invention is used to scan the retina for medical purposes, for example, it is essential that the doctor know which portion of the retina is being scanned. It may also be necessary for the doctor to direct the patient to change his angle of gaze in order to scan a specific area of the retina. Hence the need for calibration to establish an origin point.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3a, 3b and 3c show schematically an embodiment in which the device is rotated to compensate for rotation of the eye so as to maintain alignment between the device and the pupil opening;

FIG. 4a shows schematically a plan view of the device optics positioned relative to a user's eye;

FIG. 4b shows the arrangement shown in FIG. 4a in spatial relationship with a spectacle frame demonstrating a volumetric gap between the user's face and the spectacle frame into which the device optics is accommodated;

FIG. 11a shows pictorially a smartphone seen by a user over a small field of view;

FIGS. 11b and 11c show pictorially the smartphone seen by a user wearing head-gear according to the invention over an extended field of view;

FIG. 11d shows pictorially line-of-sight selection of a menu icon displayed on the extended smartphone image;

FIGS. 12a and 12b show respective images of a smartphone when viewed using headgear according to the invention in conditions of high ambient light as compared with a conventional view;

FIG. 13 is a block diagram showing schematically an object orientation accessory for use with headgear according to the invention;

DETAILED DESCRIPTION OF EMBODIMENTS

In the following description of some embodiments, identical components that appear in more than one figure or that share similar functionality will be referenced by identical reference symbols.

Figure 1:
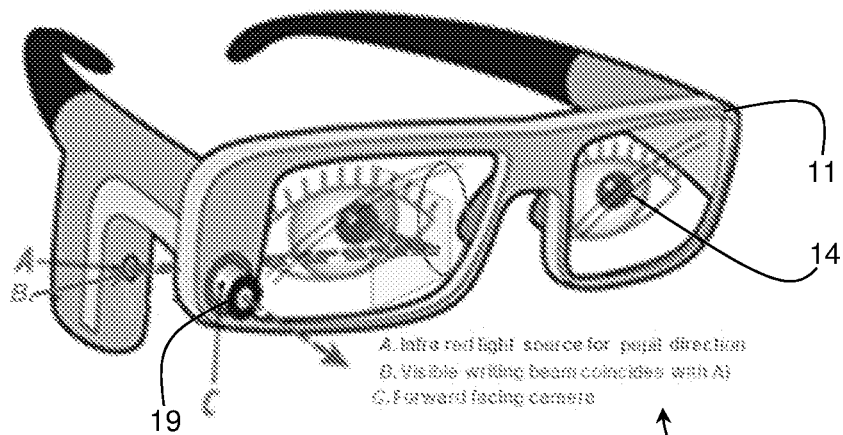
FIG. 1 is a pictorial representation of a tracking scanning laser optics device according to an embodiment of the invention mounted in a spectacle frame.
Figure 2:
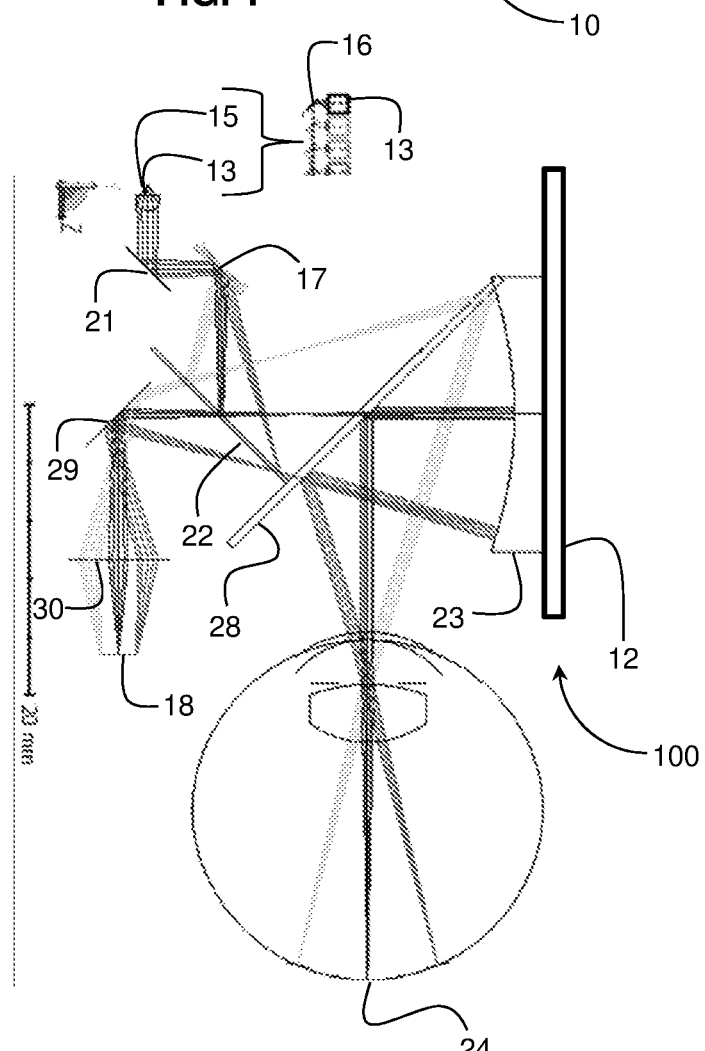
FIG. 2 shows schematically the optical construction of the tracking scanning laser optics device.

Referring to FIGS. 1 and 2 there is shown a tracking scanning laser optics device according to an embodiment of the invention mounted in a spectacle frame 11. The device 10 includes a mounting unit 12 configured for attachment to the spectacle frame 11 and to which the various optical components of the device are fixed. For the sake of illustration, the mounting unit 12 is shown in FIG. 2 schematically. In practice, as described below, it may be a suitable bracket or a frame or partial frame that supports the optical components in correct relative disposition and which can be retrofitted to a spectacle frame either during manufacture of the spectacle frame or by an optician or other technician prior to sale to an end-user.

A low-energy infrared diode 13 constituting an invisible light source is supported by the mounting unit 12 for directing invisible light through a pupil 14 of the user for scanning and imaging a portion of the retina. Red, Green and Blue (R, G, B) laser diodes constituting visible light sources are supported by the mounting unit 12 substantially collinear with each other and with the infrared diode 13 for directing visible light through the pupil for writing on to the retina within the same portion. In practice this is achieved by directing each light source from the side through a respective semi-transparent beam-splitter 16 oriented at an angle of 45° to the light emitted by the light source. The infrared diode 13 and the laser diodes 15 may be mounted in the side-bar of the spectacle frame. The beam splitters reflect the light through 90° so that the reflected beams are orthogonal to the source and each passes through the next beam-splitter mounted directly in line such that the invisible and visible light beams are collinear. For the sake of abundant caution, it is noted here that in the priority application IL 269809, color drawings were filed and representative beams of light were shown in red, blue and green so that the fracture of these beams caused by rotation of the eye could be more easily discerned. Each beam is a composite of all four light sources and the color-coding was intended only to allow the three representative beams of light to be more easily identified.

A micro-mechanical scanner 17 constituting 2-D scanning optics is supported by the mounting unit 12 for scanning the portion of the retina with the invisible and visible light. An imaging device 18, such as a CCD sensor is supported by the mounting unit 12 for receiving at least the invisible light reflected by the retina and storing an image thereof, which is used to compute the pupil's angle of gaze relative to a known reference. A camera 19 constituting a calibration means operates in conjunction with the micromechanical scanner 17 for determining an origin in 2-D space for serving as a reference point for identifying a location of the scanned portion of the retina. In some embodiments, the mounting unit 12 is rigidly attached to the spectacle frame 11 in which case the camera 19 may also be supported by the mounting unit 12. However, in accordance with other embodiments, the mounting unit 12 is capable of limited angular rotation relative to the spectacle frame 11. In this case, a micro-motor 20 (shown in FIG. 5 and described with reference to FIGS. 8a-8c) is mounted on the spectacle frame 11 and the mounting unit 12 is rotatably coupled to the motor.

FIG. 2 shows schematically the optical system is greater detail. Thus, the invisible and visible light beams are directed collinearly to a first beam-splitter 21, which reflects them through 90° to the micro-mechanical scanner 17. Under control of a control unit (not shown), the scanner 17 reflects the light beams along two mutually orthogonal axes so as to cover a planar semi-reflecting second beam splitter 22, shown only in cross-section in the figure and whose surface is parallel to the first beam-splitter 21. Part of the light impinging on each point of the second beam splitter 22 is reflected to a convex spherical mirror 23 and is reflected thereby toward a planar semi-reflecting third beam splitter 28 whose surface is perpendicular to that of the second beam splitter 22. Part of the light impinging on each point of the third beam splitter 28 is reflected toward the eye and passes through the pupil to the retina 24. Thus, as the micromechanical scanner 17 directs the light across the surface of the second beam splitter 22, it is redirected by the spherical mirror 23 and the third beam splitter 28 and scans a corresponding area of the retina. This allows us to write on to the surface of the retina within a portion covered by the scanning optics.

But we also need to be able to convey at least the infrared light impinging on the retina back to the imaging device 18 since this allows us to determine the direction of gaze. The manner in which this is achieved will now be explained. The light that is reflected by the spherical mirror 23 is only partially reflected by the third beam splitter 28. The remainder passes through the third beam splitter 28 and converges on to a reflector 29 disposed parallel to the third beam splitter 28, such that it is reflected toward a focusing lens 30 which focuses it on to the imaging device 18.

Having described the optics of the device 10, we will now describe an example of use of the device for retinal scanning and conveying results to a doctor, possibly located remotely from the patient. Typically, the doctor needs to scan different areas of the retina each having biometrics of particular relevance for specific diseases. To this end, the device must first be calibrated so that the scanning optics can image a specific portion of the retina. This is done by the patient looking at a fixed point on a well-defined object and entering its location into a controller, which is not shown but will be described later with reference to a different application. When the pupil is directed substantially straight ahead, an object in space is brought into view by slight rotational movement of the eye, which moves the pupil into the line of sight of the object. An image of the object is then formed on an area of the retina that will be central when the pupil looks exactly straight ahead, but will be shifted laterally and/or vertically when the person shifts his gaze to the left or right or up or down. Within the context of the invention, it is to be understood that the user's gaze is determined only by motion of the pupil without rotation of the user's head. Once a specific point in space has been aligned with the user's line of sight, any known coordinate on the retina can serve as an origin point with respect to which movement of the pupil can be correlated.

Calibration requires the doctor or other operative to mark a reference point on the retina, by writing a reticle or equivalent marker defining an origin on to the retina and instructing the patient to direct his gaze to a fixed and easily identifiable point in space, which we will refer to as a calibration point, and to adjust his gaze until the two points are coincident. Any shift of the user's gaze causing a rotational shift of the pupil can be determined because the Infrared light directed through the pupil and reflected back will strike a different point on the image sensor 18. The resultant shift allows any change in the direction of gaze to be quantified, and serves to determine a corresponding shift on the retina relative to the predetermined origin.

This allows us to write to any portion of the retina since the micro-mechanical scanner 17 can be controlled so as to direct light on to any desired point on the retina relative to the known origin. At the same time, invisible light reflected from different coordinates of the retina allow the direction of gaze to be determined. Furthermore, when used for remote retinal scanning, after first calibrating the device, the doctor can scan other portions of the retina by instructing the patient to look right/left or up/down. But he can also write another reference point on to the retina corresponding to an origin portion of a new portion to be scanned and then instruct the user to direct his gaze on the calibration point until the two points are coincident.

In all cases the invisible infrared light directed to the scanned portion of the retina will be absorbed more readily by the blood vessels within the retina than the surrounding tissue and so are easily identified from an analysis of the reflected light received by the imaging device 18.

The calibration unit is part of the external processing unit that also serves as the controller for the scanning assembly, the electronics, the micro-motors and video control. Calibration performs two separate tasks: (i) projects a virtual image with visible light on to the retina and then compares the image that the eye sees with the image projected. If the images coincide, then the virtual and real images are calibrated. This is achieved by controlled movement of the mirror until the real and virtual images overlap.

But having done this, we also need to calibrate the external image (which is now aligned with the virtual image) with the angle of gaze. The reason for this is that if the pupil is directed straight ahead an image will be formed on a first portion of the retina. If it now moves through an angle of say 10°, a different image will be formed on a different portion of the retina—and so we need to know where the new portion of the retina is in order to be able to project a virtual image onto the correct portion. To do this, we image the reflected invisible light with the CCD imaging device, which gives us a picture or map of the retina. So when the user looks straight ahead, we can mark a point on the retina corresponding to the optic disk, being the central portion of the retina from where all the blood vessels and nerves exit to the brain. If the pupil now rotates, the scanning mirror will need also to rotate to maintain the pupil in its line of sight and the invisible light will be reflected by the mirror to a different point on the retina. In order to be able to write to this new point we need to know where it is relative to the origin.

Calibration thus implements the following procedure:
(a) image the invisible light reflected from the retina to obtain an image of the structure of the retina;
(b) process the image to identify the optic disk where the optic nerve meets the retina;
(c) mark an origin point on the retina corresponding to the center of the optic disk when the user gazes straight ahead;
(d) determine a second point on the retina corresponding to angular movement of the pupil that is tracked by rotating the 2-D scanning optics through a known angle (α); and
(e) correlate the known angle (α) of rotation of the 2-D scanning optics to a measured displacement (d) on the retina between the origin point and the second point.

Once this is done, visible light may be directed to a desired point on the retina displaced a distance D from the origin point by rotating the 2-D scanning optics through an angle (β) where $$\beta = \left(\frac{D}{d}\right)\alpha.$$

The above arrangement works well for the type of application described for two reasons that to some extent overlap. First, because in low ambient light conditions as found indoors the pupil dilates sufficiently to allow the invisible and visible light to enter the pupil and strike the retina, at least over a sufficiently large area of the retina to be useful. Secondly, because for so long as the user's gaze is directed over a fairly limited angular field of view, the pupil opening will be sufficiently wide to allow the light to enter the pupil and exit therefrom to the imaging device. Of course, this essential requirement can be enhanced using drops to cause the pupils to dilate as is customarily done in eye clinics.

But there other applications of the invention particularly outdoor uses where the ambient light intensity is such that the pupil constricts to such an extent as to render it impossible to image more than a tiny portion of the retina. This drawback is further exacerbated by the fact that any slight rotation of the eye moves the pupil out of alignment with the light sources. As the pupil opening constricts, there is less leeway for light to enter the pupil obliquely when the eye is even only slightly rotated. Therefore, in accordance with another embodiment the invention having a micro-motor 20, the tracking scanning laser optics device 10 is rotated relative to the spectacle frame so as to direct the infrared and visible light at progressively oblique angles of the retina and thereby progressively scan successive portions of the retina.

FIGS. 3a, 3b and 3c show schematically three successive scans. The configuration of FIG. 3a is the same as shown and described with reference to FIG. 2, namely where the user's gaze is directed straight ahead. In this case, a central portion of the retina is scanned as explained above. In FIG. 3b the user has directed his gaze to the left causing his eye to rotate by about 2° thereby bringing the pupil out of alignment with the light sources. This misalignment is compensated for by rotating the scanning device 10 in the same direction as the eye whereby the light sources remain aligned with the center of the pupil. FIG. 3b shows an advanced stage of movement where the user has directed his gaze even further to the left causing his eye to rotate still more, the resulting misalignment being compensated for by rotating the scanning device 10 by an equivalent amount.

Once the device is calibrated as explained above, misalignment between the pupil opening and the light sources is easily determined because the imaging device 18 stops receiving any signal. Since it is obviously known which points on the imaging device were illuminated prior to signal loss, the direction of rotation of the pupil is easily inferred. This allows the controller to send adjustment signals to the micro-motor 20 so that the device rotation tracks the rotation of the eye and the imaging device 18 is continually illuminated.

FIG. 4a shows schematically a plan view of the device optics positioned relative to a user's eye. FIG. 4b shows the arrangement shown in FIG. 4a in spatial relationship with a spectacle frame 11 demonstrating the feasibility of the invention. FIGS. 5a to 5d show different views of the spectacle frame and the device optics. Thus, the spectacle frame comprises two mounts 35, 35' for supporting lenses connected by a bridge 36 that is supported on the user's nose. Typically, the mounts 35, 35' are frames, which accommodate the lenses and whose outer respective edges 37 support the side-arms 38 but the lenses can also be suspended under the upper part of the spectacle frame. The gap between the inner surface of the spectacle frame and the user's face 39 (shown in shadow in FIGS. 5b and 5c) is normally negligible in the region of the bridge, but for most spectacle frames having only slight curvature, the gap increases as one progresses from the bridge 36 toward the outer edge 37 of the frame owing to the more dominant curvature of the user's face. There is thereby formed in front of the user's face a volumetric gap 40 of generally trapezoidal cross-section, which abuts a volumetric gap 41 formed between each side of the face and the proximate side-arm, and the combined gap volumetric 42 shown schematically in FIG. 6 whose dimensions in mm are shown is used to accommodate optical components of varying dimensions.

Figure 5B:
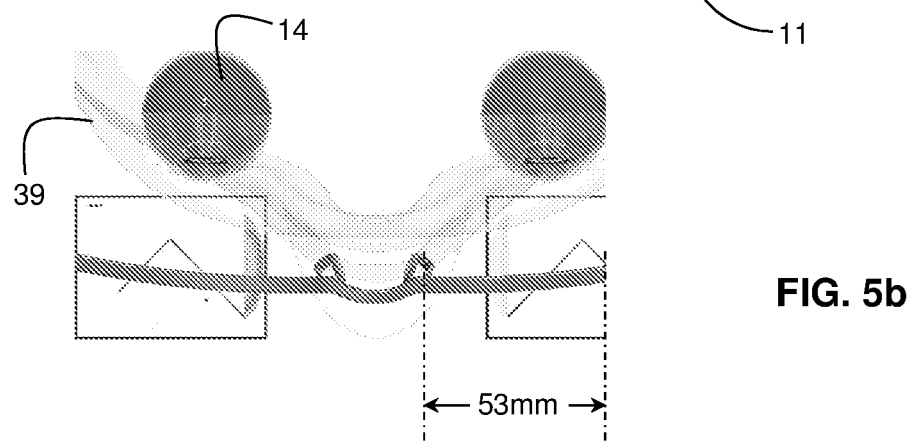
Figure 5C:
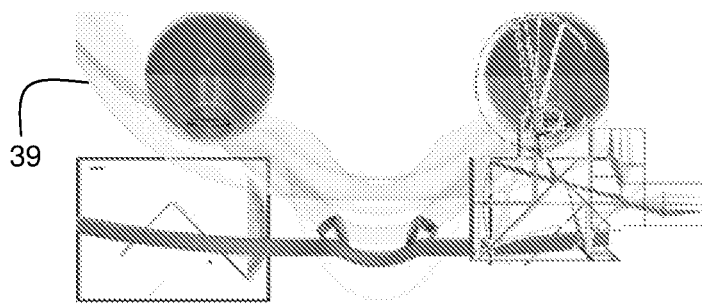
Figure 5D:
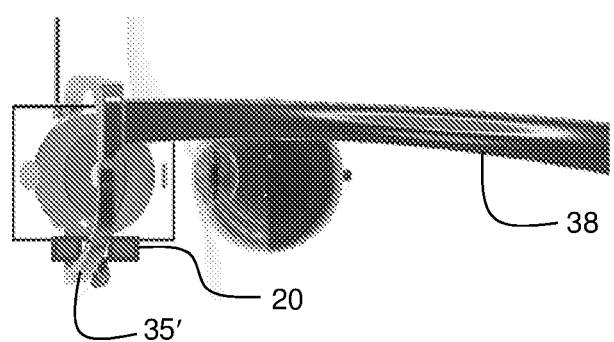
Figure 6:
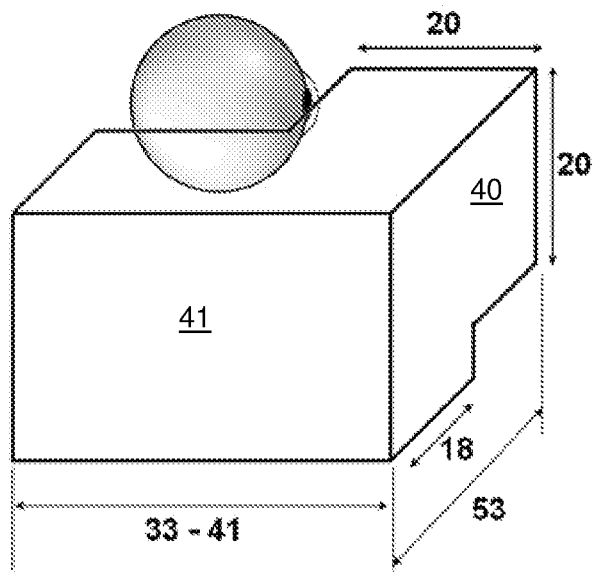
FIG. 6 is a schematic representation of a volumetric gap formed between the user's face and spectacle frame and which is used to accommodate the device optics.

Spectacle frames come in different dimensions to suit people of varying size. Our feasibility study was based on a medium frame having a width of 53 mm from one end of the bridge 36 to the proximate side-arm as shown in FIG. 5b. FIG. 6 shows the combined volumetric gap 42 for the right eye in the form of inner and outer juxtaposed cubes, a symmetrical arrangement being provided for the left eye. The inner and outer cubes are respectively labelled 40 and 41 since they are equivalent to the two volumetric gaps described earlier. The distance from the front of the cornea to the rear surface of the corrective lens (shown in the figure by the horizontal distance of 20 mm) is known as the vertex distance and, for a given user, is affected by where the spectacle frame sits on the user's nose. Spectacle lenses are usually designed on the assumption that the bridge of the spectacle frame sits snugly at the top of the nose, but it is not uncommon for it to slip down. In some embodiments, the invention increases the vertex distance by intentionally seating the bridge lower down the user's nose thereby allowing the depth of the inner volumetric gap 40 to be enlarged, albeit by only a few millimeters but this can be significant when space is at a premium.

Figure 7:
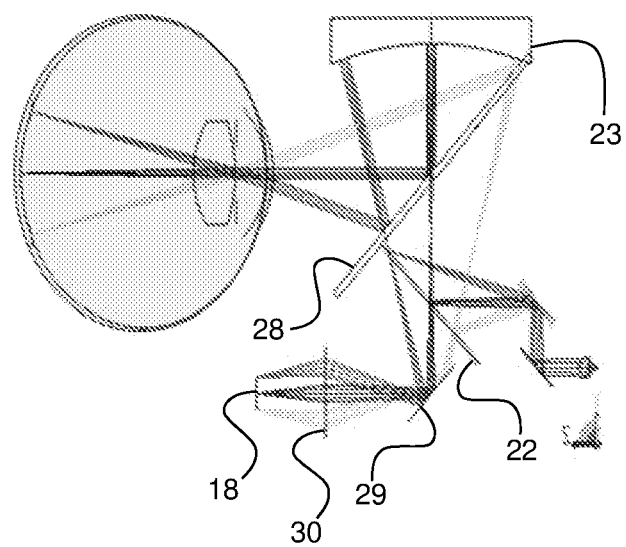
FIG. 7 shows schematically the device optics shown in FIG. 4a rotated through 90° for demonstrating its being accommodated within the volumetric gap of FIG. 6.

To further demonstrate the feasibility of the optical arrangement shown in FIG. 4a, FIG. 7 shows the same optical arrangement rotated through 90°, so that it appears in the same orientation as FIG. 6. The spherical mirror 23 and the third beam splitter 28 are located in the inner cube 40. Specifically, the spherical mirror 23 and the third beam splitter 28 are mounted on opposite sides of each opening of the spectacle frame. In one embodiment, the scanner 17 is mounted proximate the bridge 36 of the spectacle frame 11 and the spherical mirror 23 is mounted proximate a side arm 38 of the spectacle frame. Alternatively, the spherical mirror 23 may be mounted proximate the bridge 36 of the spectacle frame 11 with the scanner 17 mounted proximate the side arm 38 of the spectacle frame.

The CCD sensor 18, the reflector 29 and the focusing lens 30 are located with the outer cube 41. The second beam splitter 22 bridges both cubes.

Figure 8A:
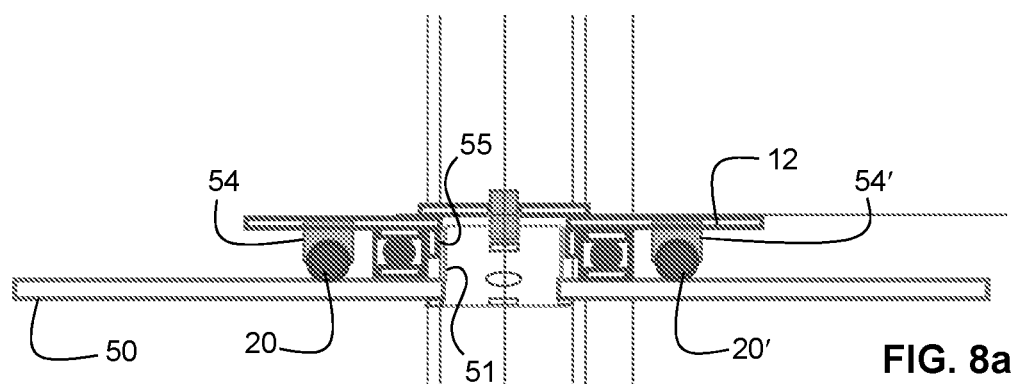
FIGS. 8a to 8c show different views of the spectacle frame and micro-motor assembly.
Figure 8B:
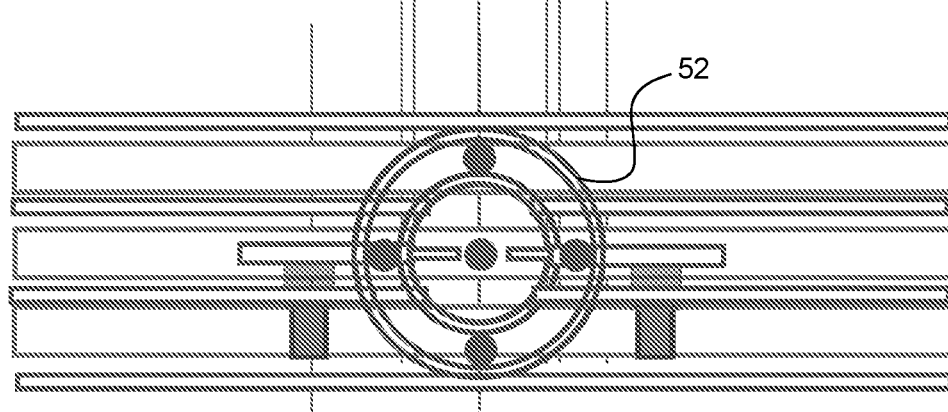
Figure 8C:
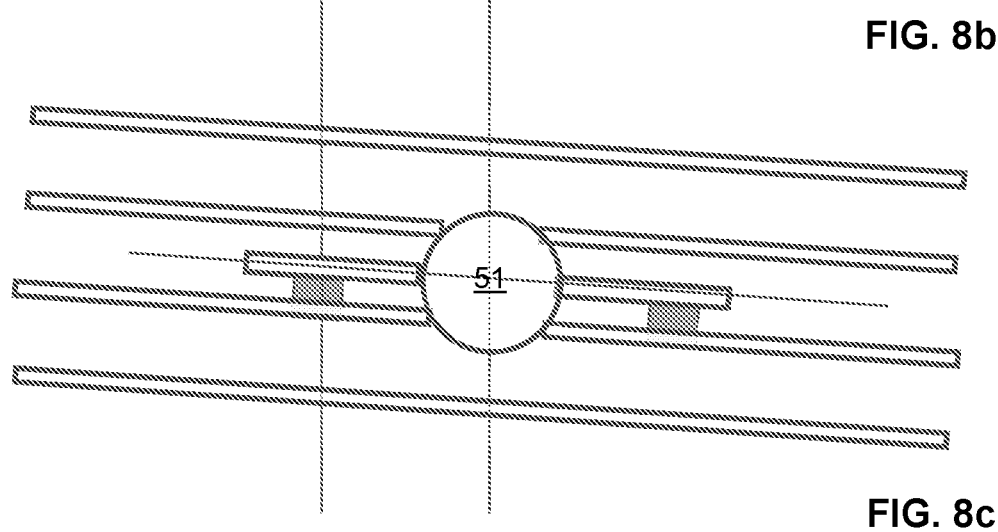

FIGS. 8a and 8b show respectively a partial front elevation and plan view of the spectacle frame and micro-motor assembly, it being noted that the figures show only one side of the spectacle frame corresponding to a single eye of the user. A symmetrical arrangement may likewise be provided for the second eye. A mounting frame 50 having a width of approximately 4 mm is attached to the lower rim of the spectacle frame or a customized frame is provided having a suitable platform for supporting the motor assembly. In order to reduce weight, the mounting frame 50 may be formed of a woven structure having slats 50a, 50b, 50c corresponding to the weft, the warp not being shown for the sake of simplicity. The mounting frame 50 has a central aperture 51, surrounding which is a bearing assembly 52 that is fixed on its lower surface to the mounting frame 50 and whose upper surface supports the mounting unit 12 on which the optical components of the scanner 17 are mounted. By such means the mounting unit 12 may rotate relative to the mounting frame 50. Rotation is achieved by two linear piezoelectric motors 20, 20' capable of executing a push-pull stroke of several millimeters and which urge against respective resilient pads 54, 54' attached to mating surfaces of the mounting frame 50. The resilient pads 54, 54' compress slightly when acting on by a pushing movement of the linear motors and transfer the linear force to a rotational force whereby the mounting frame 50 rotates on the bearing assembly 52. The direction of rotation is determined by which of the two motors pushes and which pulls under control of a suitably programmed processing unit (not shown), which in practice may be external to the eyeglasses and electrically coupled to the motors 20, 20' via a conductive slip ring 55 which is brushed by a contact fixed to the mounting frame and thus operates as a commutator. In similar manner electrical power and video signals are input to and extracted from the optical components supported on the mounting unit 12 without the need to connect dedicated wires from the motors and the optical components to an external processor and battery. This allows the motor assembly and the scanner assembly to be retrofitted as an off-the-shelf unit on to a suitably adapted spectacle frame without the need for soldering or otherwise attaching connecting wires to the motor assembly and the scanner assembly.

The mounting unit 12 supports the infrared diode 13 and the CCD sensor 18, whose power and video signals are coupled to the external processor via the slip ring 55 so that as the pupil rotates and is tracked by the scanning assembly, the corresponding image of the retina is imaged by the CCD sensor 18 and fed to the external processor for subsequent processing and analysis.

Having described the scanning device we will now describe various applications that may be implemented using the device, which exploit the very high retinal scanning accuracy of the invention. During trial tests it was determined that the retinal scan could be measured to within a resolution of 8 µm. Therefore, assuming that the focal length of the eye when focused at infinity is 25 mm, this translates to an angular resolution of:

$$\frac{0.008}{25} = 0.00032 \text{ radian}$$

This demonstrates that the angular resolution of the retinal scanning provided by the invention is 32 mrad, i.e. that the scanning device can measure angular displacement of the pupil to within an accuracy of less than 0.5 mrad.

Figure 9:
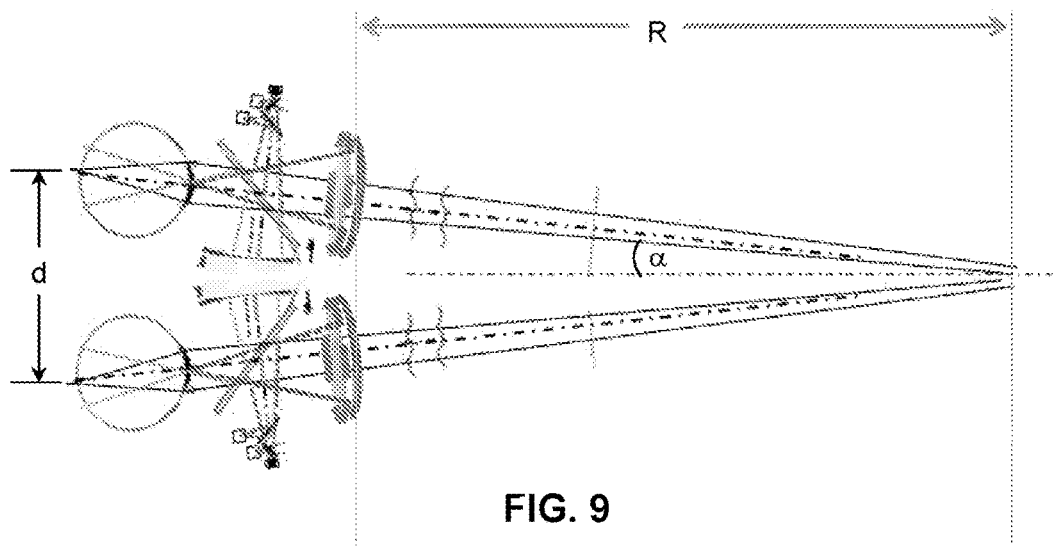
FIG. 9 shows an application of the invention for measuring range of an object.

FIG. 9 shows schematically a rangefinder that allows a user wearing a device according to the invention to look at a distant object and determine its range, i.e. the distance of the object from the user. When focusing on a distant object while looking directly at the object, the respective pupil of each eye rotates through a small angle until both lines of sight converge. As noted above, the angular movement of each pupil results in the respective image being formed on a portion of the retina that is displaced from the calibrated origin and the displacement allows the angular rotation of each pupil to be determined.

Since the inter-pupillary distance is known, the range of the object is easily calculated as follows:

$$\tan(\alpha) = \frac{d}{2R}$$

$$R = \frac{d}{2\tan(\alpha)}$$

where: d is the inter-pupillary distance,
R is the Range, and
α is the measured angular rotation of the pupil.

When the range is large, angle α is small and tan (α) is approximately equal to the measure of α in radians, i.e.

$$R \approx \frac{d}{2\alpha}$$

The device invention according to the invention can measure the pupillary angle with an accuracy of several tenths of a radian as opposed to conventional devices based on corneal measurement whose accuracy is 0.5° corresponding to 8.5 mrad, resulting in a 20-fold improvement in accuracy.

Figure 10:
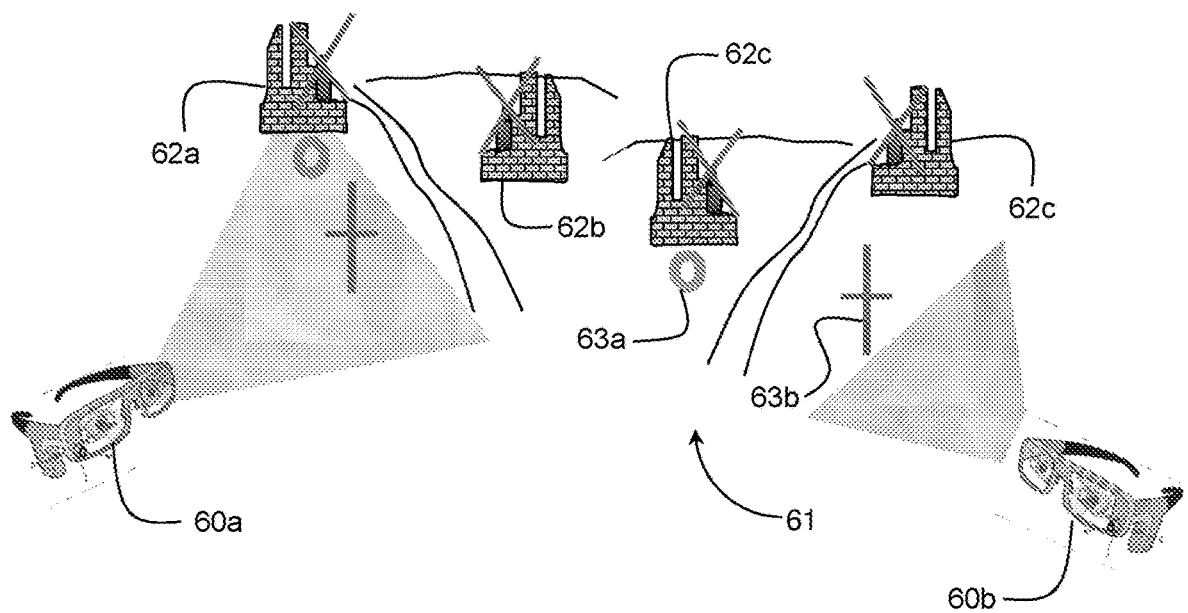
FIG. 10 shows pictorially an application of the invention for remotely monitoring a battlefield and providing commands to soldiers.

FIG. 10 shows pictorially an application of the invention used by a command control center remotely monitoring a battlefield to direct one or more substantially stationary soldiers 60a, 60b each wearing headgear according to the invention to fire on specified targets in a firing range 61 containing two or more targets 62a-62d. The command control center is in wireless communication with all the soldiers and remote control is implemented as follows:
(a) allocating to each soldier a respective unique identity and display symbol (63a, 63);
(b) obtaining an image of the battlefield that shows respective locations of all soldiers;
(c) directing each soldier in turn to gaze on at least one other soldier and determining a respective distance between each pair of soldiers;
(d) directing each soldier in turn to gaze on all the targets in firing range of said soldier;
(e) repeating (c) and (d) until respective distances between all the soldiers are known thereby enabling a plan of the battlefield to be determined identifying the soldiers and the targets in firing range of each soldier; and
(f) for each soldier in turn determining a suitable target among all the targets in range for the respective soldier and conveying the pre-allocated display symbol so that it is written on to the soldier's retina at a location thereof that points toward the selected target.

Communication between the command center and the soldiers' headgear is effected wirelessly, for example via RF or IR. The command center may be remote from the battlefield while local commands to each soldier may be conveyed by a commander in the field. The commander or remote controller may be equipped with a computer having a touchscreen, allowing an operator thereof to select a target by touch and to touch an image of the selected soldier whereby the appropriate symbol is written on to the retina of the selected soldier at a location that identifies the selected target.

FIG. 11a shows pictorially a conventional smartphone 65 that is hand-held at a distance of say 50 cm from a user 66. Assuming that the width of the smartphone is 7 cm, the field of view extends over an angle of whose screen subtends an angle of view of approximately 8° thereby forming an image on only a narrow portion of the user's retina. Each menu icon 67 occupies only a small fraction of the image and the more icons that are displayed, the smaller they appear. This imposes a practical limit to the number of icons that can be meaningfully displayed simultaneously.

FIGS. 11b and 11c depict use of the headgear according to the invention, whereby this limitation is overcome by scanning a high-resolution digital image of the screen over an extended angle so as to form an image over a larger portion of the retina, thus presenting a magnified virtual image 68 that appears to emanate from a remote location. This allows the user to see comfortably a virtual image 69 of the smartphone having many more icons than can be accommodated under normal use.

FIG. 11d shows an enlarged detail 70 of the smartphone screen wherein by tracking the pupil when the user fixes her line of sight 71 on a desired icon, the icon can be selected by the user issuing a suitable control that convey a signal to the headgear, whereby the selected icon can be identified according to a known layout of the screen and the angular location thereon of the selected icon relative to a predetermined origin.

FIG. 12a shows yet a further advantage in that since the screen of the smartphone is a virtual image written directly on to the retina, its visibility does not depend on image contrast and the display is legible even in full daylight. FIG. 12b shows a conventional smartphone where the icons are illegible.

Figure 14:
FIG. 14 shows pictorially use of headgear worn by a soldier used with the accessory of FIG. 13 for assisting in aiming a weapon.

FIG. 13 shows schematically an object orientation accessory 80 that may be used in conjunction with headgear according to the invention worn by a soldier shown in FIG. 14 for assisting in aiming a weapon and accurately shooting from the hip a remote target, without bringing the weapon to the eye for aiming as it is done conventionally. The object orientation accessory 80 is mounted on a side-arm of the headgear and allows determination of 3-D spherical coordinates (r, θ, φ) of an object 81 in space remote from an eye of the user (such as a hand-held weapon). The object orientation accessory 80 comprises two laser diodes 82, 82' each configured for directing respective beams of light 83, 83' toward different points 84, 84' on the object. Two detectors 85, 85' are provided each configured for detecting respective reflections 86, 86' of the beams from the corresponding points on the object and an area sensor 87 is provided for imaging a surface of the object. A processor 88 coupled to the detectors 85, 85' and to the area sensor 87 is configured to measure respective distances ($r_1$, $r_2$) propagated by the beams 83, 83' and determine therefrom the yaw (θ) of the object relative to the headgear, the processor being further configured to scan the image sensor and determine therefrom the pitch (φ) of the object relative to the headgear.

Figure 5A:
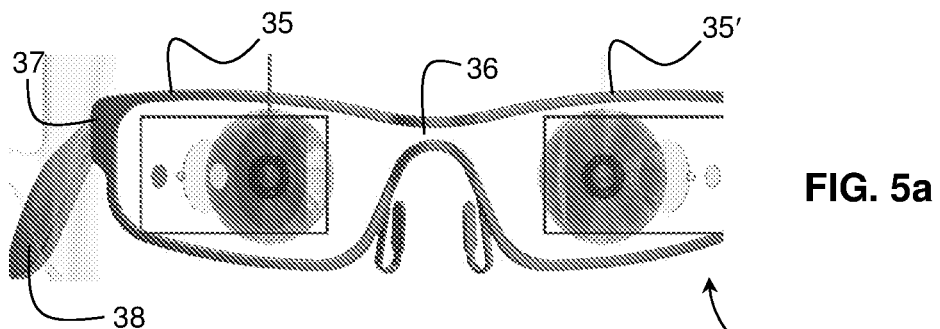
FIGS. 5a to 5d show different views of the spectacle frame and the device optics.

When the headgear is realized by spectacles as shown in FIG. 5a, the laser diodes 82, 82', detectors 85, 85' and the area sensor 87 may be mounted in the side-arms 38 of the spectacle frame 11 in such manner that the laser diodes 82, 82', detectors 85, 85' are directed to the weapon. To improve sensitivity, a suitable light-sensitive film 90 (shown in FIG. 14) may be attached to a surface of the weapon, so that when the weapon is held in proper orientation for shooting, the light-sensitive film is directed to the side-arm of the spectacle frame. In use, two target symbols are presented to the soldier's eye on a head mounted display (HMD). The first symbol represents either the direction of the pupil of the soldier's eye or the direction of a reference line on the display, while the second symbol represents the orientation of the gun with respect to the first symbol. In this way the soldier is able to match the two target symbols and shoot so as to hit the target without using the weapon's sights, which hide the field of view and could endanger the soldier. The same technique can be extended to allow the soldier to direct his weapon round a corner without exposing himself, provided only that the light-sensitive surface of the weapon remains within line of sight with the laser diodes and the detectors.

The same principle can be also applied to a camera fitted with a telephoto lens used to photograph events that appear in sequence at a distance, allowing a photographer to take photographs of several events in succession, which is not possible if the camera viewfinder is used because it hides the total field of view. For example, a wildlife photographer who wants to photograph birds in flight suffers from essentially the same problem as the sharp-shooter tracking an enemy soldier (albeit, of course, with radically different consequences). Photographers are also apt to lose track of the bird if they are constrained to hold the camera to their eye and to track the bird through the telephoto lens. The invention provides an additional degree of freedom to the photographer, who can now hold the camera and attached telephoto lens at chest height and track the bird by eye, while adjusting the orientation of the camera and telephoto lens so that the bird remains in line of sight of the camera lens.

Figure 15:
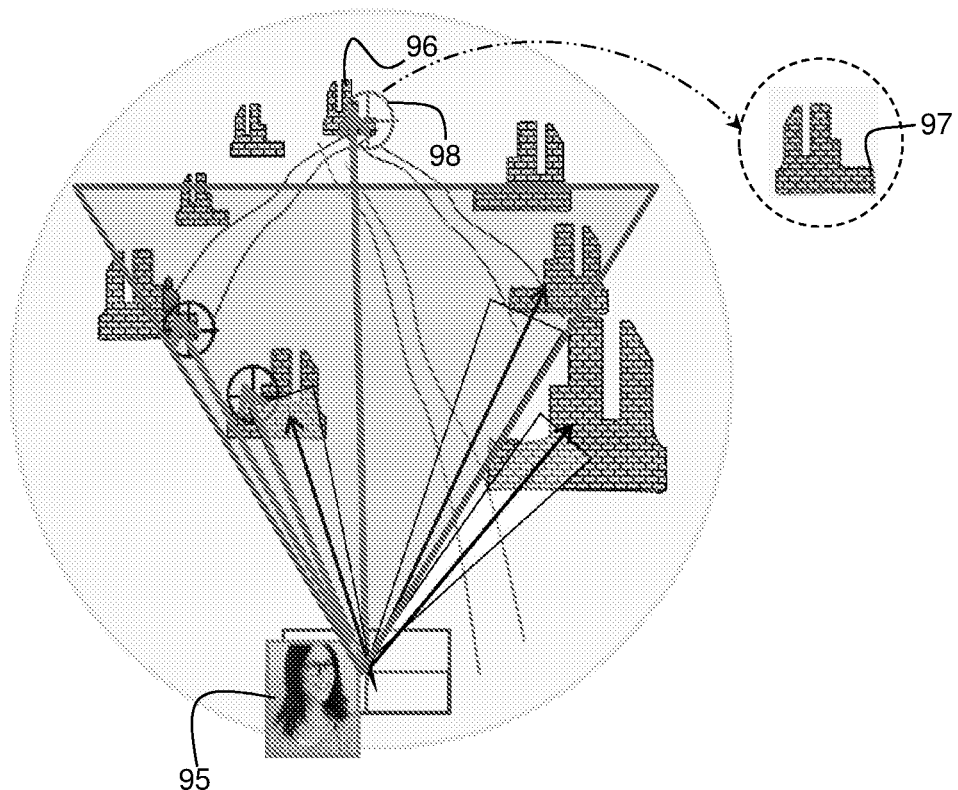
FIG. 15 shows pictorially use of the invention for accurate navigation with no GPS in open space.

FIG. 15 shows pictorially use of the invention for accurate navigation with no GPS in open space. It is assumed that we have an accurate topographic map at high resolution of the area such as Street View™. It is further assumed that we have image processing software that can identify edges or points of reference on selected objects. In use, under control of a software application coupled to the user's headgear as described above, the user is directed to set his line of sight on a distinctive landmark in the distant scene, such as a building, tree, pylon etc. The user can select either a single object in the distant landscape having at least three distinctive features, or alternatively three different objects each having a single distinctive feature, or a mixture. What is important is for the user to be able to align his or her line of sight with three distinct features in the distant scene and to identify these features to the tracking software. In the figure, the user 95 directs her gaze on to a distant building 96 having distinctive edges and, under control of a software application, which may be a smartphone application or a suitably programmed hand-held computer or PDA etc., signals to the software application the selected building. This may be done using a dedicated software key in the portable device, typically using a touchscreen. But it can also be a hardware device such as mouse button or equivalent. The software identifies one or more distinctive features such as the corner 97 and then superimposes a guide mark 98 having a reticle that is aligned with the identified feature. The user 95 now aligns her line of sight with the guide mark 98 and signals to the software application that her gaze is precisely aligned with the feature 97. The scanning device in the user's headgear determines the exact angle of gaze from a pre-calibration normal (as explained above) and is thereby able to correlate the precise location in space of the identified feature with a coordinate on the user's retina. This same process is repeated at least twice so that in total at least three distinctive features in space are identified and their precise locations are correlated with known coordinates on the user's retina.

Using triangulation, it is now possible to compute the user's location relative to the selected landmark and map the user's gaze with the distant scene. When the user now directs her line of sight to any other feature in the scene, the software by measuring the angle of gaze using the scanning device, can determine exactly where in space the user is looking. Concomitantly, the user may identify to the software application a landmark to which she requires directions, and the software can determine a suitable route and direct her accordingly. This is done without the need to know her precise location in space and therefore does not require GPS.

Figure 16:
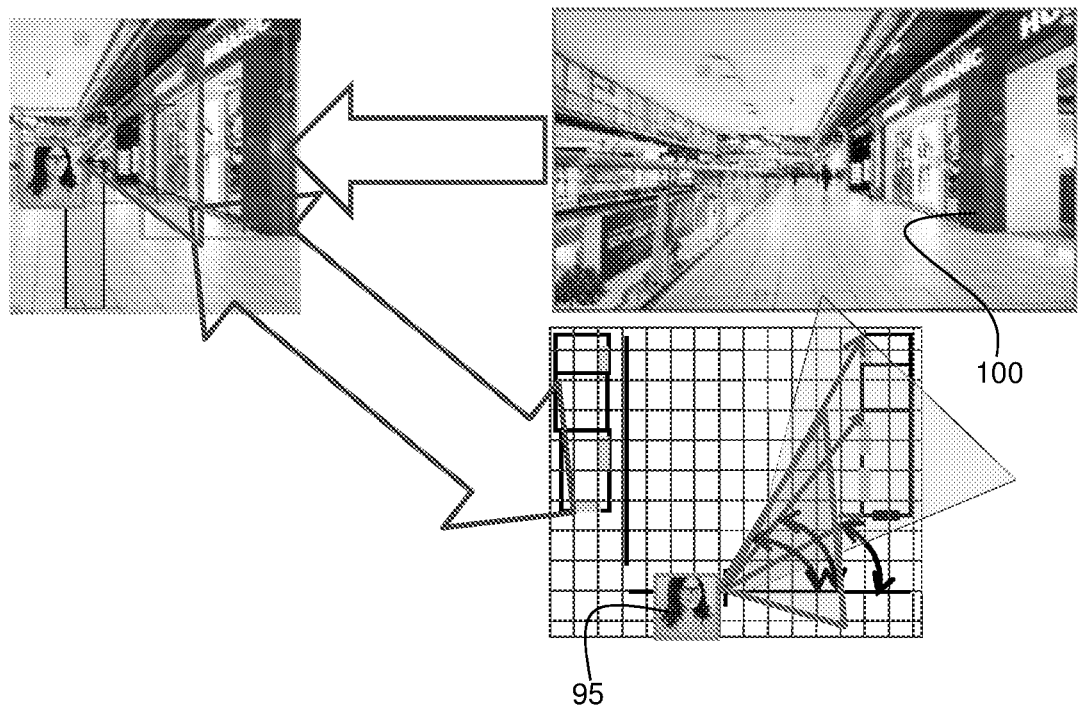
FIG. 16 shows pictorially use of the invention for accurate navigation with no
GPS in closed-in space.
Figure 17:
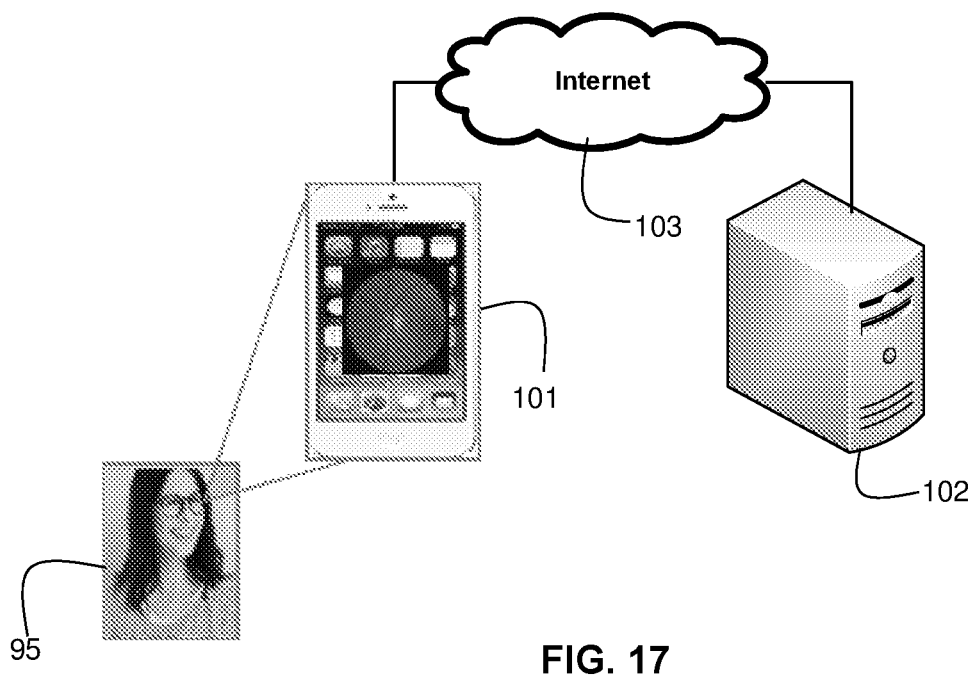
FIG. 17 shows pictorially use of the invention for ambulatory monitoring of retinal scans.

FIG. 16 shows pictorially an extension of the above technique for accurate navigation with no GPS in closed-in space such as a shopping mall. Again, it is assumed that the inside of the shopping mall is precisely mapped. The user 95 identifies to the software application in her smartphone a building 100 such as a shop. The software application identifies distinctive features of the building and displays guide marks at clearly defined geometric features thereof, each of which the user aligns in her line of sight and confirms alignment under control of the software application. This is done for at least three features whereupon the software is able to compute the user's location relative to the selected building. As in FIG. 15, the user can select any other building in the shopping mall under control of the software application and the application is now able to direct her using simple visual or vocal commands FIG. 17 shows pictorially use of the invention for ambulatory monitoring of retinal scans where a user 95 wearing headgear according to the invention performs a retinal scan at home under direction of a software application, using a computer device such as a smartphone 101 and for conveying the retinal scan to a remote server 102 over the Internet 103. An ophthalmologist located remote from the user receives the retinal scan and can remotely write a guide mark to her retina for directing her to align her sight with the guide mark. The resulting rotation of the pupil is tracked by the 2-D scanning device and thereby allows a different portion of the retina to be scanned. By such means multiple retinal scans can be obtained without the need for the user to attend the doctor's surgery in person.

Figure 18A:
FIGS. 18a and 18b are pictorial representations comparing conventional control of augmented reality with improved control provided in conjunction with a tracking device according to the invention.
Figure 18A:
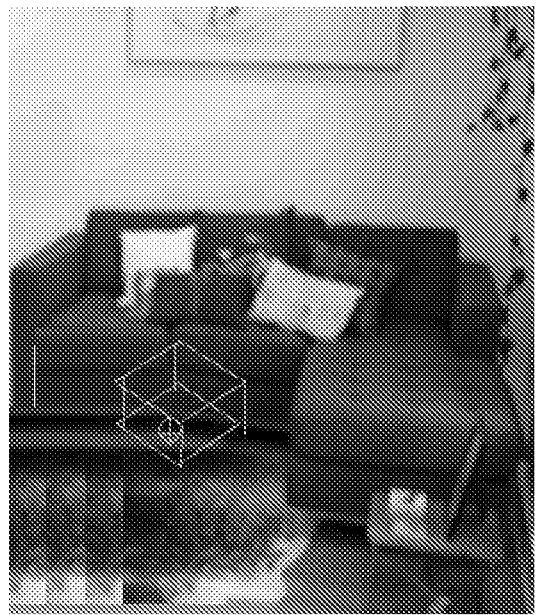
Figure 18B:
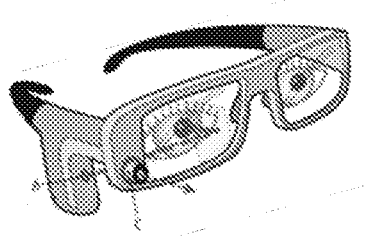

FIGS. 18*a* and 18*b* are pictorial representations comparing conventional control of augmented reality with improved control provided in conjunction with a tracking device according to the invention. Thus, as shown in a conventional AR scenario depicted in FIG. 18*a*, the user points to a selected object that he wants to move. In doing so, his finger obscures the image. The invention allows a user wearing the tracking device according to the invention to track the object and to select it when it is aligned with his direction of gaze as shown pictorially in FIG. 18*b*. The AR application software operates in conjunction with the tracking device to identify the selected object and can follow the user's gaze to relocate it in a new position identified by the user's line of sight.

Figure 19:
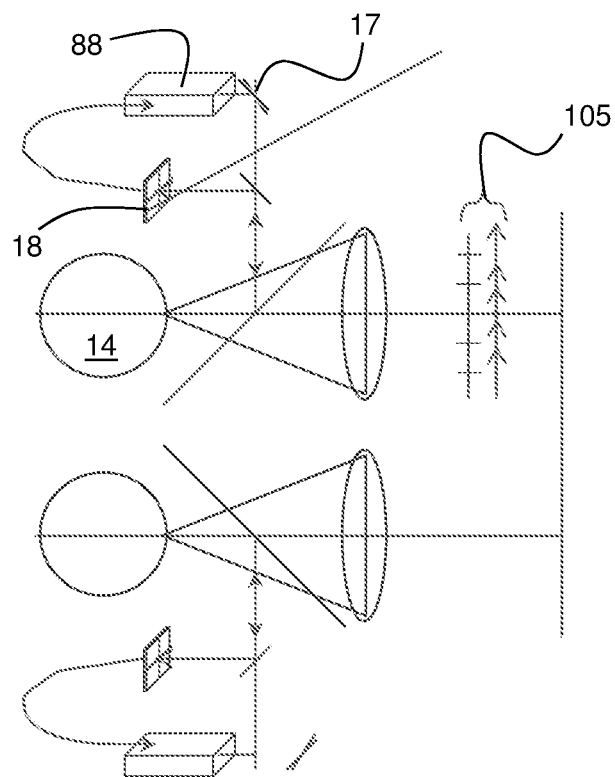
FIG. 19 is a schematic representation showing use of the invention for automatic correction of eye vision using IR scanning of the retina and for increasing system magnification without changing system lens.

FIG. 19 is a schematic representation showing use of the invention for automatic correction of eye vision using IR scanning of the retina and for increasing system magnification without changing system lens. If the user's eyesight is imperfect, a blurred or out-of-focus image of an object viewed by the eye will be formed on the retina. Normally, this is corrected by mounting an external convex or concave lens close to the eye that causes the light from the object to be focused on the retina. The invention operates as follows to provide automated correction of impairments. The optical scanner 17 operates to direct the visible LED light on to the retina thus creating an image of a virtual object located at infinity. But aberrations of the eye will result in the image being blurred also when writing with the IR laser on the retina and the reflected beam also contributes to the aberrations by traversing the eye lens. Therefore the blur which the eye sees with or without the spectacle lens appears in the image on the CCD sensor 18. To avoid this, the system shown in FIG. 19 includes an electronic shutter 105 comprising a pair of polarizing elements 105' and 105" whose respective polarizations may be controlled electronically by the processor 88. When the respective polarizations of the elements 105' and 105" are the same, the shutter 105 is optically transparent and the user sees a normal real image of the external scene. When the respective polarizations of the elements 105' and 105" are mutually orthogonal, the shutter 105 is optically opaque and the user sees only the virtual image written to the retina. This virtual image is captured by the camera 19 (shown in FIG. 1) and is focused on to the retina 24 via the scanning device through a focusing lens (not shown) that may be mounted in the spectacle frame or in proper spatial relationship therewith. The focusing lens is such that the virtual image is precisely focused on to the retina regardless of the eye's aberrations. It is now possible to reconstruct the blur analytically by comparing the well-focused image with the optical shutter 105 closed with the impaired image as seen with the optical shutter 105 open. After reconstructing the aberration analytically we can calculate how to change the scan of the object in order to minimize the blur. This may be done by adjusting field of view and resolution in order to produce a virtual image having more pixels and thus appearing sharper than would otherwise be obtained.

Similarly, to change the magnification of the system we change the field of view and the scanning angle and the scanner resolution accordingly. Specifically, to increase magnification, we reduce the field of view and increase the resolution. Resolution is a function of the scanning density of the scanner 17.

The system of FIG. 19 may also be used to automatically control the focal length of a liquid correction lens, so as to ensure that the image focused by the liquid lens on to the user's retina is sharp. In this case, the user does not see a virtual image but sees a real image of a scene through the liquid correction lens, whose focal length is adjusted in real time to produce a well-focused image on the retina.

Other uses of the invention include alerting a user wearing the headgear of an imminent danger that manifests itself in involuntary departure from a predetermined direction of gaze. For example, tracking software can determine that a motorist's gaze is wandering erratically and alert him that he is falling asleep at the wheel. In another application, a vehicle guidance system that detects an obstacle ahead can operate in conjunction with the tracking device in the motorist's headgear and alert him if he directs his gaze away from the obstacle.

In another application, conference attendees can participate remotely in an organized teleconference. Images of each attendee are conveyed to each participant and projected on to the retina of each so that they see all attendees at the same time. Each participant has a unique symbol allocated by the conference organizer and the chairman can direct each when to speak either vocally or visually. This can be done by writing an invitation to speak on to the retina of the invited participant; or by displaying on a screen seen by all attendees the unique symbol identifying the invited participant.

In the optical system described with reference to FIGS. 3a, 3b and 3c, the whole of the scanner device is rotated in order to compensate for rotation of the eye which, if not corrected, would prevent the light beams from entering the pupil. This requires that the device be rotated relative to the headgear, typically constituted by the spectacle frame and in the system described facilitates rotation in a single plane thus compensating only for eye rotation about a single axis: most typical a vertical axis corresponding to left to right movement of the pupil. It also of course requires that the optics be mounted in a module that is then rotatably attached by a motor to the spectacle frame.

Figure 20:
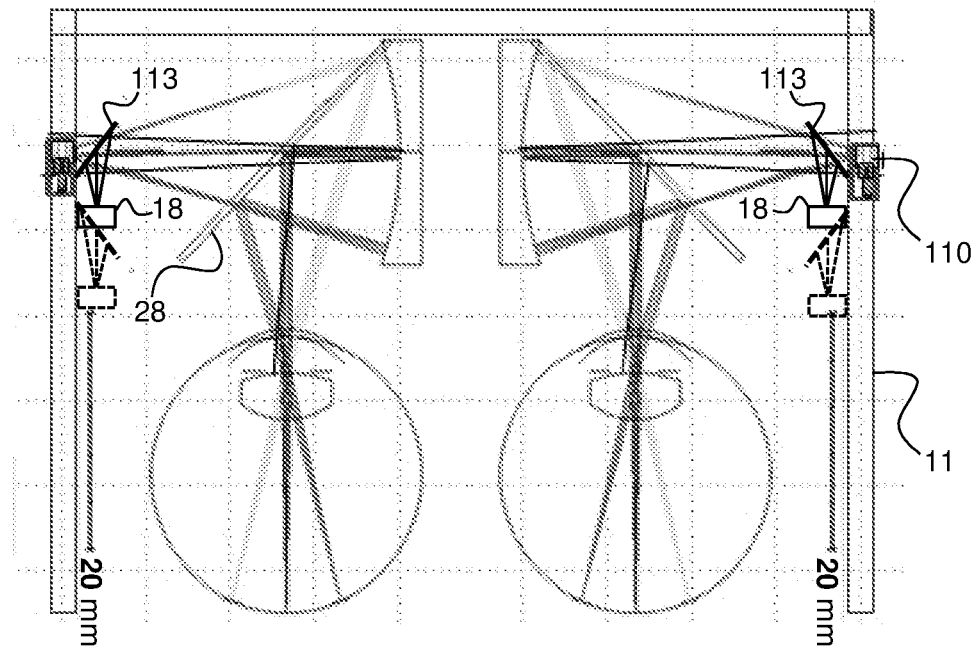
FIG. 20 shows schematically an alternative embodiment for compensating for rotation of the eye so as to maintain alignment between the device and the pupil opening.

FIG. 20 shows schematically an alternative embodiment for compensating for rotation of the eye so as to maintain alignment between the device and the pupil opening. A respective module 110 is attached to each side-arm of the spectacle frame 11 and includes a pair of miniature linear motors that move sets of optical components along mutually orthogonal axes to adjust the point of focus of the light reflected by the convex spherical mirror 23 so that the point of focus remains aligned with the pupil.

Figure 21:
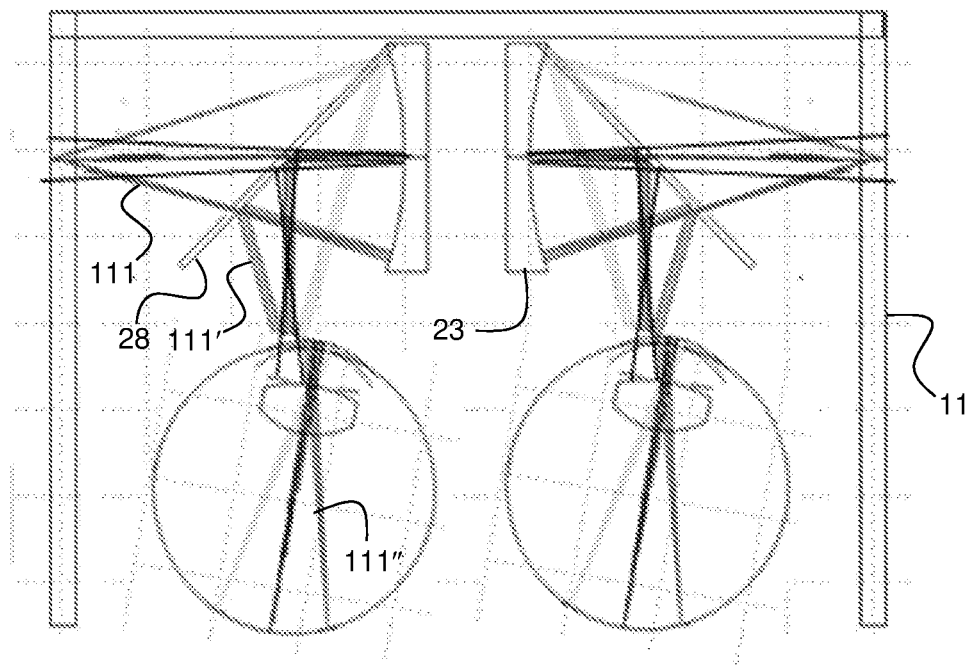
FIG. 21 shows schematically optical misalignment causes by rotation of the eye.

FIG. 21 shows schematically optical misalignment causes by rotation of the eye. Thus, if we consider the beam of light 111 that is reflected by the mirror 23, it is seen that it strikes the beam splitter 28 and is reflected thereby as a reflected beam 111' toward the eye where it enters the pupil as beam 111" which is focused on the retina. But when the pupil moves out of alignment with the reflected beam 111', it is seen that the beams 111' and 111" appear to be fractured or misaligned. As will be explained below with particular reference to FIGS. 24a and 24b, the module 110 effectively re-aligns the beams thus ensuring that the reflected beam 111' remains aligned with the pupil regardless of eye movement.

Figure 22A:
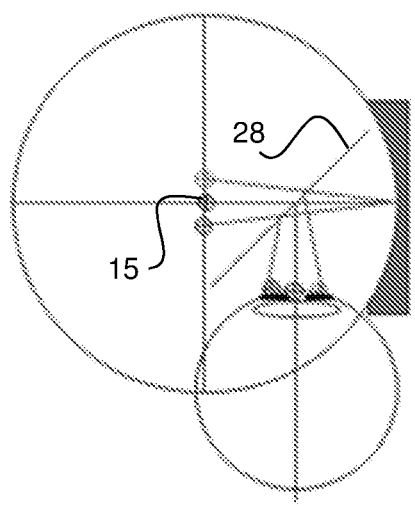
FIGS. 22a, 22b and 22c are optical ray diagrams explaining how rotation of the eye is determined.
Figure 22B:
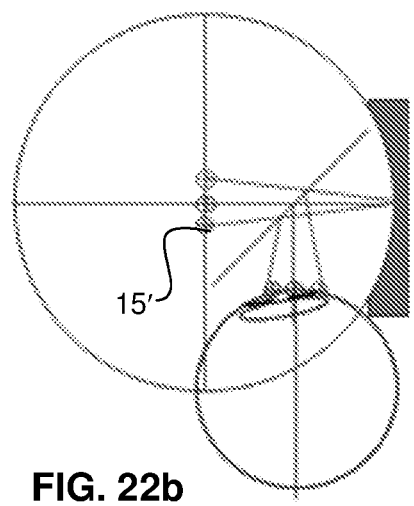
Figure 22C:
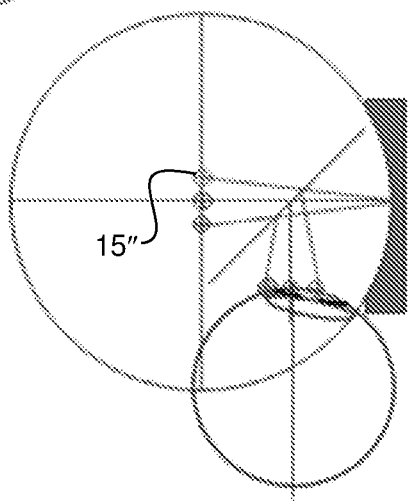

FIGS. 22a, 22b and 22c are optical ray diagrams explaining how rotation of the eye is determined. Thus, in FIG. 22a the pupil is directed straight ahead, such that light from the middle light source 15 passes through the beam splitter 28, is reflected by the convex spherical mirror 23, strikes the beam splitter 28 and is reflected through 90° where it enters the pupil directly. FIG. 22b shows the situation where the eye has rotated to the left so that the pupil is no longer aligned with the light from the middle light source 15, which consequently strikes the iris rather than entering the pupil. However, it is seen that light from the lower light source 15' does now enter the pupil. FIG. 22c shows the situation where the eye has rotated to the right and light from the upper light source 15" enters the pupil. Each of the light sources is a combination of Red, Blue and Green visible light and invisible infrared. As seen in FIG. 20, the infrared light enters the pupil, strikes the retina and is reflected back by the blood vessels within the retina toward a beam splitter 113, which redirects parts of the light to the imaging device 18. The light reflected by the retina is diffuse and the beam splitter 113 can be of sufficiently large area to collect most of the reflected light, while allowing some to pass through to the module 110. Alternatively, the detector 18 may be mounted lower down in conjunction with a full reflector shown in dotted outline, so as to allow light reflected by the retina to reach the module directly via the beam splitter 28. Owing to its being diffuse, some of the light reflected by the retina will still reach the reflector but not as much as would reach it when a beam splitter is used.

In either case, the beam splitter (or reflector) 113 and the detector are miniature components allowing for an extremely compact arrangement that may easily be mounted in the side-arm of the spectacle frame. For ease of description, we have only considered rotation of the eye about a vertical axis i.e. left to right. But the same principles apply to rotation of the eye about a horizontal axis, i.e. up and down, it being noted that the module 110 compensates for rotation in both directions as well as simultaneous rotation about both axes.

Figure 23:
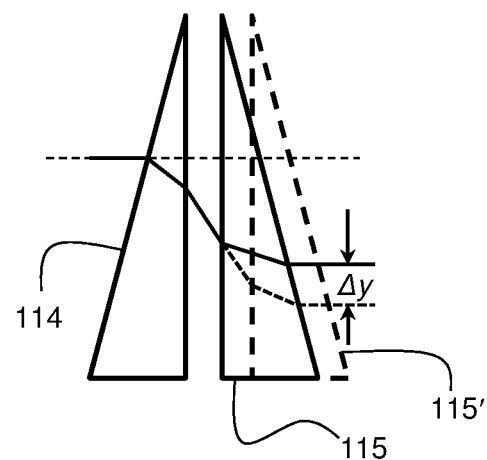
FIG. 23 shows schematically a detail of an optical system that compensates for misalignment caused by rotation of the eye.

FIG. 23 shows schematically a detail of part of the module comprising a pair of back to back right-angle prisms 114 and 115 configured for relative lateral movement by a linear motor (not shown). In a first position, a light beam entering the first prism 114 horizontally is refracted at opposing faces and strikes the vertical face of the second prism 115 wherein it is again refracted at opposing faces and exits horizontally. When the second prism is moved slightly to the right as denoted by the prism 115' shown in dotted-line, the beam exiting the first prism 114 enters the second prism 115' lower down its vertical face and so exits from the opposite face displaced vertically by an amount Ay. A first miniature linear motor (not shown) is operatively coupled to the second prism 115 for moving it toward or away from the first prism 114 as required as will now be explained with reference to FIGS. 24a and 24b showing schematically details of the module 110 and its spatial disposition relative to the light sources 13 and 15, the micro-mechanical scanner 17 and the convex spherical mirror 23.

Figure 24A:
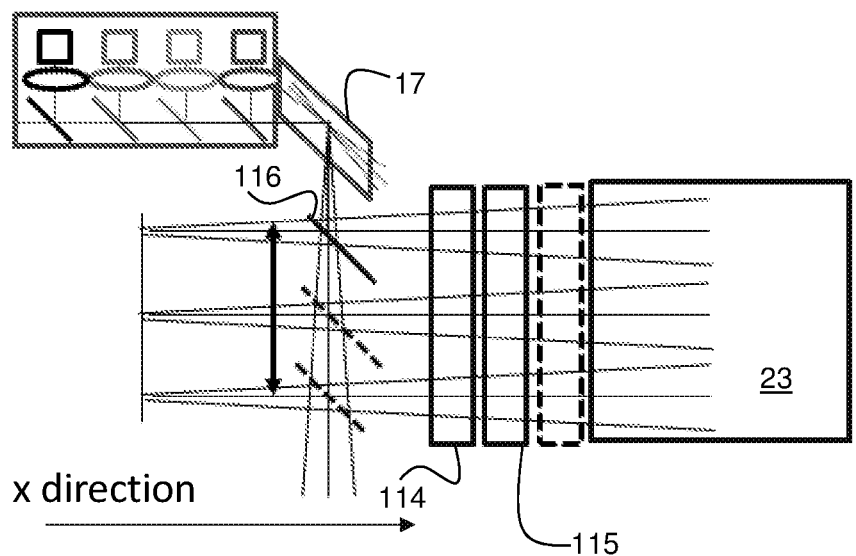
FIGS. 24a and 24b show schematically details of the optical system.
Figure 24B:
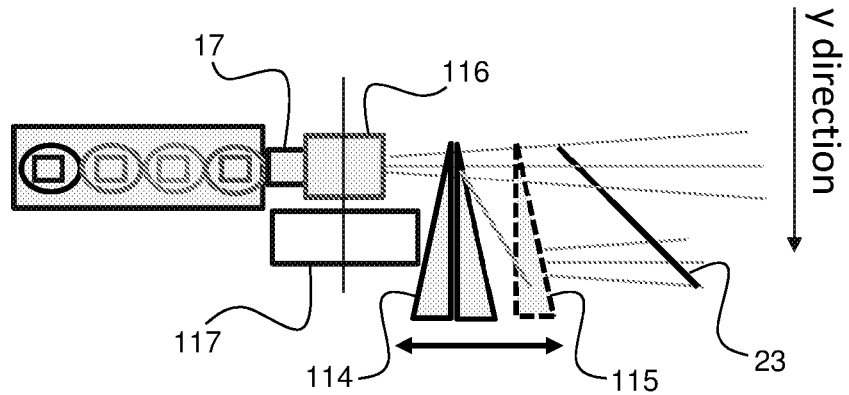

FIGS. 24a and 24b show respectively details of the module and associated optical components as seen from two mutually orthogonal axes. Thus, FIG. 24a shows the optical components in a direction x along the side-bar of the spectacle frame; while FIG. 24a shows the optical components in a direction y normal to the plane of the side-bar (i.e. directed into the paper). A mirror 116 is disposed downstream of the scanner 17 and is coupled to a second linear motor 117 for moving the mirror in either direction along the y-axis. The prisms 114 and 115 shown in FIG. 24b are located between the convex spherical mirror 23 and the mirror 116. Displacement of the mirror 116 shifts the point of focus in a plane normal to the pupil in first direction while displacement of the prism 115 shifts the point of focus in the same plane in second direction perpendicular to the first direction. So by displacing either or both the prism 115 and the mirror 116, the beam reflected by the beam splitter 28 may be redirected toward the pupil regardless of motion of the pupil caused by up/down and/or right/left motion. Furthermore, correction may be effected very quickly and the optical components can all be built into the side-bars of the spectacle frame, which serve as an integral mounting unit thus obviating the need for their being supported on a separate mounting unit. As explained above, the blood vessels of the retina are imaged by the invisible infrared light on the imaging device 18. Comparison between successive image frames allows the angular rotation of the eye about the two orthogonal axes to be computed. This information is then used to move the prism 115 and the mirror 116 by appropriate amounts to re-align the light reflected by the beam splitter 28 toward the pupil.

The description of the above embodiments is not intended to be limiting, the scope of protection being provided only by the appended claims, which are to be regarded as an integral part of the description.

It will be appreciated that while the scanning and tracking device is preferably dimensioned for mounting on to a regular spectacle frame, it may be manufactured as a separate item and as such may be mounted in other headgear. For example, it can be fitted to a head-mounted augmented reality or virtual reality system or to a pilot's or sniper's helmet according to use.

It will also be understood that some of the features of the invention may be a suitably programmed computer device. Likewise, the invention contemplates a machine readable program for executing the method of the invention. The invention further contemplates a machine-readable memory tangibly embodying a program of instructions executable by the machine for executing the method of the invention.

Summary of Combinations:

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

However, for the sake of abundant clarity and to provide unambiguous support for multiple dependencies in jurisdictions where they are permitted the invention encompasses the following statements:

Embodiment 1

A tracking scanning laser optics device configured for mounting in headgear having at least one opening for positioning in front of an eye of a user, said tracking scanning laser optics device comprising:

a mounting unit integral with or configured for attachment to the headgear, an invisible light source supported by the mounting unit for directing invisible light through a pupil of the user for scanning and imaging a portion of the retina, at least one visible light source supported by the mounting unit for directing visible light through said pupil for writing on to the retina within said portion, 2-D scanning optics supported by the mounting unit for scanning said portion of the retina with the invisible and visible light, an imaging device supported by the mounting unit for receiving at least the invisible light reflected by said portion of the retina and storing an image thereof, and a calibration unit operative in conjunction with the 2-D scanning optics for determining an origin in 2-D space for serving as a reference point for identifying a location of said portion within the retina.

Embodiment 2

The device according to embodiment 1, wherein the calibration unit is configured to:
(a) project a virtual image with visible light on to the retina;
(b) compare the real image that the eye sees with virtual the image projected; and
(c) adjust the 2-D scanning optics until the images coincide.

Embodiment 3

The device according to embodiment 1 or 2, wherein the calibration unit is configured to:
(d) image the invisible light reflected from the retina to obtain an image of the structure of the retina;

(e) process said image to identify the optic disk where the optic nerve meets the retina;

(f) mark an origin point on the retina corresponding to the center of the optic disk when the user gazes straight ahead;

(g) determining a second point on the retina corresponding to angular movement of the pupil that is tracked by rotating the 2-D scanning optics through a known angle (α); and (h) correlating the known angle (α) of rotation of the 2-D scanning optics to a measured displacement (d) on the retina between the origin point and the second point;

whereby visible light may be directed to a desired point on the retina displaced a distance D from the origin point by rotating the 2-D scanning optics through an angle (β) given by $$\left(\frac{D}{d}\right)\alpha.$$

Embodiment 4

The device according to any one of embodiments 1 to 3, wherein the mounting unit is separate from the headgear and further including a motor for rotating the mounting unit relative to the headgear to track movement of the pupil relative to the headgear.

Embodiment 5

The device according to any one of embodiments 1 to 4, wherein:

the headgear is a pair of eyeglasses comprising a spectacle frame defining a pair of openings each for positioning in front of respective eyes of a user and having a pair of side-arms, the spectacle frame has a low profile having a maximum depth not exceeding 5 mm Embodiment 6

The device according to embodiment 5, comprising:

an invisible light source (11) supported by the mounting unit (12) for directing invisible light through a pupil (14) of the user for scanning and imaging a portion of the retina, visible light sources (15) supported by the mounting unit (12) for directing visible light collinearly with the invisible light through the pupil for writing on to the retina within the same portion, a micro-mechanical scanner (17) supported by the mounting unit (12) for scanning the portion of the retina with the invisible and visible light, an imaging device (18) supported by the mounting unit (12) for receiving at least the invisible light reflected by the retina and storing an image thereof, and a camera (19) operating in conjunction with the micro-mechanical scanner (17) for determining an origin in 2-D space for serving as a reference point for identifying a location of the scanned portion of the retina.

Embodiment 7

The device according to embodiment 6, wherein the visible light sources (15) includes Red, Blue and Green color components all of which are configured to direct light mutually collinearly with the invisible light.

Embodiment 8

The device according to embodiment 7, wherein:

each of the visible light sources is directed from a side of the spectacle frame through a respective semi-transparent beam-splitter (16) oriented at an angle of 45° to the light emitted by the light source, the beam splitters reflect the light through 90° so that the reflected beams are orthogonal to the light sources and each passes through a successive beam-splitter mounted directly in line such that the invisible and visible light beams are collinear.

Embodiment 9

The device according to embodiment 7 or 8, wherein:

a first beam-splitter (21) for reflecting the invisible and visible light beams to a them through 90° to the micro-mechanical scanner (17), a control unit for directing the scanner (17) to reflect the light beams along two mutually orthogonal axes so as to cover a planar semi-reflecting second beam splitter (22) whose surface is parallel to the first beam-splitter (21), a convex spherical mirror (23) supported by the mounting plate (12) for receiving light impinging on each point of the second beam splitter (22) and reflected thereby, and a planar semi-reflecting third beam splitter (28) disposed between the scanner (17) and the spherical mirror (23) for receiving on a surface thereof light reflected by the second beam splitter (22) and reflecting said light toward the eye through the pupil to the retina (24).

Embodiment 10

The device according to any one of embodiments 5 to 9, wherein the scanner (17) and the spherical mirror (23) are mounted on opposite sides of each opening of the spectacle frame.

Embodiment 11

The device according to embodiment 10, wherein the scanner (17) is mounted proximate a bridge (36) of the spectacle frame (11) and the spherical mirror (23) is mounted proximate a side arm (38) of the spectacle frame.

Embodiment 12

The device according to embodiment 10, wherein the spherical mirror (23) is mounted proximate a bridge (36) of the spectacle frame (11) and the scanner (17) is mounted proximate a side arm (38) of the spectacle frame.

Embodiment 13

The device according to any one of embodiments 6 to 12, wherein the mounting unit (12) is rotatably coupled to the spectacle frame (11) by a micro-motor (20) for enabling limited angular rotation of the mounting unit relative to the spectacle frame.

Embodiment 14

The device according to any one of embodiments 6 to 12, further including a module (110) supported by the mounting unit (12) and including first and second miniature linear motors (117) that move sets of optical components along mutually orthogonal axes for tracking rotation of the eye and maintaining alignment with the pupil.

Embodiment 15

The device according to embodiment 14, wherein:
the module (110) includes a pair of back to back right-angle first and second prisms (114, 115) configured for relative lateral movement by the first linear motor,
an entry beam of light is directed by the scanner (17) to a vertical face of the first prism (114), is refracted at opposing faces and strikes a vertical face of the second prism (115) wherein it is again refracted at opposing faces and exits as an exit beam parallel to the entry beam;
lateral movement the second prism induces a vertical displacement ($\Delta y$) of the exit beam.

Embodiment 16

The device according to embodiment 14 or 15, further including:
a mirror (116) disposed downstream of the scanner (17) and coupled to the second linear motor 117 for moving the mirror in a direction and by an amount that maintains alignment with the pupil.

Embodiment 17

The device according to any one of embodiments 6 to 16, further including:
an electronic shutter (105) for controlling whether the user sees a real image of a scene or a virtual image as seen by the imaging device (19),
a processor (88) for receiving respective impaired and sharp images obtained with the electronic shutter (105) open and closed, the processor being configured to compare the sharp image with the impaired image and to calculate how to change the scan of the object in order to reduce blur.

Embodiment 18

The device according to embodiment 17, wherein the electronic shutter (105) comprises a pair of polarizing elements (105', 105") whose respective polarizations are controlled electronically by the processor (88).

Embodiment 19

The device according to embodiment 17 or 18, wherein the processor is configured to reduce blur by adjusting field of view and resolution in order to produce a virtual image having more pixels and thus appearing sharper than would otherwise be obtained.

Embodiment 20

The device according to any one of embodiments 17 to 19, wherein the processor is configured to change magnification by changing field of view and scanning angle to adjust scanner resolution of the scanner.

Embodiment 21

The device according to embodiment 17, further including a liquid correction lens through which an impaired view is obtained and wherein the processor is configured to receive respective impaired and sharp images obtained with the electronic shutter (105) open and closed, to compare the sharp image with the impaired image and to adjust the focal length of the liquid lens in order to reduce blur.

Embodiment 22

Headgear comprising:
a frame defining a pair of openings each for positioning in front of respective eyes of a user, and
at least one tracking scanning laser optics device according to any one of the preceding embodiments, said device being mounted by the respective mounting unit to the headgear for scanning and imaging a portion of the retina of a respective eye of the user.

Embodiment 23

The headgear according to embodiment 22, wherein the frame is a spectacle frame having a pair of side-arms.

Embodiment 24

The headgear according to embodiment 22 or 23, further including a motor supported by the frame for rotating the mounting unit to track movement of the pupil relative to the headgear.

Embodiment 25

The headgear according to embodiment 22 or 23, further including (11) a module (110) supported by the mounting unit (12) and including first and second miniature linear motors (117) that move sets of optical components along mutually orthogonal axes for tracking rotation of the eye and maintaining alignment with the pupil.

Embodiment 26

The headgear according to embodiment 25, wherein:
the module includes a pair of back to back right-angle first and second prisms (114, 115) configured for relative lateral movement by the first linear motor,
an entry beam of light is directed by the scanner (17) to a vertical face of the first prism (114), is refracted at opposing faces and strikes a vertical face of the second prism (115) wherein it is again refracted at opposing faces and exits as an exit beam parallel to the entry beam;
lateral movement the second prism induces a vertical displacement ($\Delta y$) of the exit beam.

Embodiment 27

The headgear according to embodiment 25 or 26, further including:
a mirror (116) disposed downstream of the scanner (17) and coupled to the second linear motor 117 for moving the mirror in a direction and by an amount that maintains alignment with the pupil.

Embodiment 28

The headgear according to any one of embodiments 22 to 27, further comprising an object orientation accessory for determining 3-D spherical coordinates (r, θ, φ) of an object in space remote from the headgear, said accessory comprising:
two laser diodes each configured for directing respective beams of light toward different points on the object,
two detectors each configured for detecting respective reflections of said beams from the corresponding points on the object,
an area sensor configured for imaging a surface of the object, and
a processor coupled to the detectors and to the area sensor and configured to measure respective distances ($r_1$, $r_2$) propagated by said beams and determine therefrom the yaw (θ) of the object relative to the headgear, the processor being further configured to scan the image sensor and determine therefrom the pitch (φ) of the object relative to the headgear.

Embodiment 29

The headgear according to embodiment 28 when dependent on embodiment 22, wherein the laser diodes, detectors and area sensor are mounted in the side-arms of the spectacle frame.

Embodiment 30

The headgear according to embodiment 28 or 29, wherein the calibration means includes a forward-looking camera mounted on the headgear for imaging a scene viewed by the user.

Embodiment 31

A method for assisting a user wearing the headgear of embodiment 28 to align a hand-held object with a point of interest in a line of sight of the user, the method comprising:
(a) imaging the scene viewed by the user;
(b) writing on the retina a first guide mark at a point corresponding to a direction of gaze of the pupil,
(c) writing on the retina a second guide mark at a point corresponding to an instantaneous orientation of the object; and
(d) while the user's gaze is fixated on the point of interest changing the orientation of the object so as to align the object with the point of interest and repeating (c) until the first and second guide marks are coincident.

Embodiment 32

A method for estimating a range (R) of a distant object in a line of sight of the user wearing the headgear of any one of embodiments 22 to 30, the method comprising:
(a) imaging the object with at least one eye;
(b) determining an angle of rotation (α) of a pupil of said eye based on the rotation of the scanning optics; and
(c) computing the range from the measured angle (α) and a predetermined inter-pupillary distance (d) according to $$R \approx \frac{d}{2\alpha}$$

where the angle (α) is in radians.

Embodiment 33

A method for remotely directing one or more stationary soldiers each wearing headgear according to any one of embodiments 22 to 30 to fire on specified targets in a battlefield containing two or more targets, each of said soldiers having a respective unique identity and display symbol, the method comprising the following steps carried out by a remote command control center:
(a) obtaining an image of the battlefield that shows respective locations of all soldiers;
(b) directing each soldier in turn to gaze on at least one other soldier and determining a respective distance between each pair of soldiers;
(c) directing each soldier in turn to gaze on all the targets in firing range of said soldier;
(d) repeating (c) and (d) until respective distances between all the soldiers are known thereby enabling a plan of the battlefield to be determined identifying the soldiers and the targets in firing range of each soldier; and
(e) for each soldier in turn determining a suitable target among all the targets in range for the respective soldier and conveying the pre-allocated display symbol so that it is written on to the soldier's retina at a location thereof that points toward the selected target.

Embodiment 34

A method for providing an enlarged view of an object to a user wearing the headgear according to any one of embodiments 22 to 30, wherein when viewed without the headgear, the object is imaged over a narrow portion of the retina, the method comprising:
(a) obtaining a digital image of the object; and
(b) writing said image over an extended portion of the retina of the user so as to present an enlarged field of view.

Embodiment 35

A method for accurate navigation of a user wearing the headgear according to any one of embodiments 22 to 30, without need of GPS in an open or confined space for which there is accessible a topographic map at high resolution, the method comprising:
(a) identifying one or more distinctive landmarks in the distant scene selected by a user;
(b) determining at least three distinctive features in total of the selected landmark or landmarks and identifying the distinctive features to the user by superimposing a guide mark on each of the distinctive features;
(c) directing the user to set her line of sight on each of said distinctive features so that the line of sight is aligned with the guide marks;
(d) measuring the user's direction of sight based on measured angular rotation of the 2-D scanning optics in the user's headgear;
(e) correlating the precise location in space of each identified feature with a coordinate on the user's retina; and
(f) computing the user's current location relative to the selected landmark and mapping the user's gaze with the open or confined space.

Embodiment 36

The method according to embodiment 35, further including:
(g) identifying a remote location in the open or confined space to which the user requires directions;

(h) determining from said topographic map a route from the user's current location to the remote location; and
(i) providing directions to the user for reaching the remote location.

Embodiment 37

A method for alerting a motorist wearing the headgear according to any one of embodiments 22 to 30, of involuntary departure from a predetermined direction of gaze, the method including:
(a) monitoring the motorist's direction of gaze;
(b) determining whether fluctuations in the direction of gaze are indicative of a potentially hazardous driving condition; and
(c) if so, alerting the motorist.

Embodiment 38

A method for controlling an augmented reality (AR) application by a user wearing the headgear according to any one of embodiments 22 to 30, the method comprising:
(a) monitoring the user's direction of gaze for identifying an object in the AR application; and
(b) following the user's direction of gaze for moving the object to a new location.

Embodiment 39

A method for remotely directing multiple mutually remote attendees at a teleconference when to speak, each remote attendee wearing headgear according to any one of embodiments 22 to 30, and each having a respective unique identity and display symbol, the method comprising the following steps carried out by a conference organizer:
(a) conveying images of each participant for projecting on to the retina of each participant so that each participant sees all participants at the same time; and
(b) directing each participant when to speak either by writing an invitation to speak on to the retina of the invited participant; or by displaying on a screen seen by all attendees the respective unique symbol identifying the invited participant.

The invention claimed is:

1. A tracking scanning laser optics device configured for mounting in headgear having at least one opening for positioning in front of an eye of a user, said tracking scanning laser optics device comprising:
a mounting unit integral with or configured for attachment to the headgear,
an invisible light source supported by the mounting unit for directing invisible light through a pupil of the user for scanning and imaging a portion of the retina,
at least one visible light source supported by the mounting unit for directing visible light through said pupil for writing on to the retina within said portion,
2-D scanning optics supported by the mounting unit for scanning said portion of the retina with the invisible and visible light,
an imaging device supported by the mounting unit for receiving at least the invisible light reflected by said portion of the retina and storing an image thereof, and
a calibration unit operative in conjunction with the 2-D scanning optics for determining an origin in 2-D space for serving as a reference point for identifying a location of said portion within the retina.

2. The device according to claim 1, wherein the calibration unit is configured to:
(a) project a virtual image with visible light on to the retina;
(b) compare the real image that the eye sees with virtual the image projected; and
(c) adjust the 2-D scanning optics until the images coincide.

3. The device according to claim 1, wherein the calibration unit is configured to:
(a) image the invisible light reflected from the retina to obtain an image of the structure of the retina;
(b) process said image to identify the optic disk where the optic nerve meets the retina;
(c) mark an origin point on the retina corresponding to the center of the optic disk when the user gazes straight ahead;
(d) determining a second point on the retina corresponding to angular movement of the pupil that is tracked by rotating the 2-D scanning optics through a known angle ($\alpha$); and
(e) correlating the known angle ($\alpha$) of rotation of the 2-D scanning optics to a measured displacement (d) on the retina between the origin point and the second point;
whereby visible light may be directed to a desired point on the retina displaced a distance D from the origin point by rotating the 2-D scanning optics through an angle ($\beta$) given by $$\left(\frac{D}{d}\right)\alpha.$$

4. The device according to claim 1, wherein the mounting unit is separate from the headgear and further including a motor for rotating the mounting unit relative to the headgear to track movement of the pupil relative to the headgear.

5. The device according to claim 1, wherein:
the headgear is a pair of eyeglasses comprising a spectacle frame defining a pair of openings each for positioning in front of respective eyes of a user and having a pair of side-arms,
the spectacle frame has a low profile having a maximum depth not exceeding 5 mm.

6. The device according to claim 5, comprising:
an invisible light source supported by the mounting unit for directing invisible light through a pupil of the user for scanning and imaging a portion of the retina,
visible light sources supported by the mounting unit for directing visible light collinearly with the invisible light through the pupil for writing on to the retina within the same portion,
a micro-mechanical scanner supported by the mounting unit for scanning the portion of the retina with the invisible and visible light,
an imaging device supported by the mounting unit for receiving at least the invisible light reflected by the retina and storing an image thereof, and
a camera operating in conjunction with the micro-mechanical scanner for determining an origin in 2-D space for serving as a reference point for identifying a location of the scanned portion of the retina.

7. The device according to claim 6, wherein the visible light sources include Red, Blue and Green color components all of which are configured to direct light mutually collinearly with the invisible light.

8. The device according to claim 7, wherein:
each of the visible light sources is directed from a side of the spectacle frame through a respective semi-transparent beam-splitter oriented at an angle of 45° to the light emitted by the light source,
the beam splitters reflect the light through 90° so that the reflected beams are orthogonal to the light sources and each passes through a successive beam-splitter mounted directly in line such that the invisible and visible light beams are collinear.

9. The device according to claim 7, wherein:
a first beam-splitter for reflecting the invisible and visible light beams through 90° to the micro-mechanical scanner,
a control unit for directing the scanner to reflect the light beams along two mutually orthogonal axes so as to cover a planar semi-reflecting second beam splitter whose surface is parallel to the first beam-splitter,
a convex spherical mirror supported by the mounting plate for receiving light impinging on each point of the second beam splitter and reflected thereby, and
a planar semi-reflecting third beam splitter disposed between the scanner and the spherical mirror for receiving on a surface thereof light reflected by the second beam splitter and reflecting said light toward the eye through the pupil to the retina.

10. The device according to claim 5, wherein the scanner and the spherical mirror are mounted on opposite sides of each opening of the spectacle frame.

11. The device according to claim 10, wherein the scanner is mounted proximate a bridge of the spectacle frame and the spherical mirror is mounted proximate a side arm of the spectacle frame.

12. The device according to claim 10, wherein the spherical mirror is mounted proximate a bridge of the spectacle frame and the scanner is mounted proximate a side arm of the spectacle frame.

13. The device according to claim 6, wherein the mounting unit is rotatably coupled to the spectacle frame by a micro-motor for enabling limited angular rotation of the mounting unit relative to the spectacle frame.

14. The device according to claim 6, further including a module supported by the mounting unit and including first and second miniature linear motors that move sets of optical components along mutually orthogonal axes for tracking rotation of the eye and maintaining alignment with the pupil.

15. The device according to claim 14, wherein:
the module includes a pair of back-to-back right-angle first and second prisms configured for relative lateral movement by the first linear motor,
an entry beam of light is directed by the scanner to a vertical face of the first prism, is refracted at opposing faces and strikes a vertical face of the second prism wherein it is again refracted at opposing faces and exits as an exit beam parallel to the entry beam;
lateral movement the second prism induces a vertical displacement (Δy) of the exit beam.

16. The device according to claim 14, further including:
a mirror disposed downstream of the scanner and coupled to the second linear motor for moving the mirror in a direction and by an amount that maintains alignment with the pupil.

17. The device according to claim 6, further including:
an electronic shutter for controlling whether the user sees a real image of a scene or a virtual image as seen by the imaging device,
a processor for receiving respective impaired and sharp images obtained with the electronic shutter open and closed, the processor being configured to compare the sharp image with the impaired image and to calculate how to change the scan of the object in order to reduce blur.

18. The device according to claim 17, wherein the electronic shutter comprises a pair of polarizing elements whose respective polarizations are controlled electronically by the processor.

19. The device according to claim 17, wherein the processor is configured to reduce blur by adjusting field of view and resolution in order to produce a virtual image having more pixels and thus appearing sharper than would otherwise be obtained.

20. The device according to claim 17, wherein the processor is configured to change magnification by changing field of view and scanning angle to adjust scanner resolution of the scanner.

21. The device according to claim 17, further including a liquid correction lens through which an impaired view is obtained and wherein the processor is configured to receive respective impaired and sharp images obtained with the electronic shutter open and closed, to compare the sharp image with the impaired image and to adjust the focal length of the liquid lens in order to reduce blur.

22. Headgear comprising:
a frame defining a pair of openings each for positioning in front of respective eyes of a user, and
at least one tracking scanning laser optics device according to claim 1, said device being mounted by the respective mounting unit to the headgear for scanning and imaging a portion of the retina of a respective eye of the user.

23. The headgear according to claim 22, wherein the frame is a spectacle frame having a pair of side-arms.

24. The headgear according to claim 22, further including a motor supported by the frame for rotating the mounting unit to track movement of the pupil relative to the headgear.

25. The headgear according to claim 22, further including a module supported by the mounting unit and including first and second miniature linear motors that move sets of optical components along mutually orthogonal axes for tracking rotation of the eye and maintaining alignment with the pupil.

26. The headgear according to claim 25, wherein:
the module includes a pair of back-to-back right-angle first and second prisms configured for relative lateral movement by the first linear motor,
an entry beam of light is directed by the scanner to a vertical face of the first prism, is refracted at opposing faces and strikes a vertical face of the second prism wherein it is again refracted at opposing faces and exits as an exit beam parallel to the entry beam;
lateral movement the second prism induces a vertical displacement (Δy) of the exit beam.

27. The headgear according to claim 25, further including:
a mirror disposed downstream of the scanner and coupled to the second linear motor 117 for moving the mirror in a direction and by an amount that maintains alignment with the pupil.

28. The headgear according to claim 22, further comprising an object orientation accessory for determining 3-D spherical coordinates (r, θ, φ) of an object in space remote from the headgear, said accessory comprising:
two laser diodes each configured for directing respective beams of light toward different points on the object, two detectors each configured for detecting respective reflections of said beams from the corresponding points on the object, an area sensor configured for imaging a surface of the object, and a processor coupled to the detectors and to the area sensor and configured to measure respective distances ($r_1$, $r_2$) propagated by said beams and determine therefrom the yaw ($\theta$) of the object relative to the headgear, the processor being further configured to scan the image sensor and determine therefrom the pitch ($\phi$) of the object relative to the headgear.

29. The headgear according to claim 28 when dependent on claim 22, wherein the laser diodes, detectors and area sensor are mounted in the side-arms of the spectacle frame.

30. The headgear according to claim 28, wherein the calibration means includes a forward-looking camera mounted on the headgear for imaging a scene viewed by the user.

31. A method for assisting a user wearing the headgear of claim 28 to align a hand-held object with a point of interest in a line of sight of the user, the method comprising:
   (a) imaging the scene viewed by the user;
   (b) writing on the retina a first guide mark at a point corresponding to a direction of gaze of the pupil,
   (c) writing on the retina a second guide mark at a point corresponding to an instantaneous orientation of the object; and
   (d) while the user's gaze is fixated on the point of interest changing the orientation of the object so as to align the object with the point of interest and repeating (c) until the first and second guide marks are coincident.

32. A method for estimating a range (R) of a distant object in a line of sight of the user wearing the headgear of claim 22, the method comprising:
   (a) imaging the object with at least one eye;
   (b) determining an angle of rotation ($\alpha$) of a pupil of said eye based on the rotation of the scanning optics; and
   (c) computing the range from the measured angle ($\alpha$) and a predetermined inter-pupillary distance (d) according to $$R \approx \frac{d}{2\alpha}$$

where the angle ($\alpha$) is in radians.

33. A method for remotely directing one or more stationary soldiers each wearing headgear according to claim 22 to fire on specified targets in a battlefield containing two or more targets, each of said soldiers having a respective unique identity and display symbol, the method comprising the following steps carried out by a remote command control center:
   (a) obtaining an image of the battlefield that shows respective locations of all soldiers;
   (b) directing each soldier in turn to gaze on at least one other soldier and determining a respective distance between each pair of soldiers;
   (c) directing each soldier in turn to gaze on all the targets in firing range of said soldier;
   (d) repeating (c) and (d) until respective distances between all the soldiers are known thereby enabling a plan of the battlefield to be determined identifying the soldiers and the targets in firing range of each soldier; and
   (e) for each soldier in turn determining a suitable target among all the targets in range for the respective soldier and conveying the pre-allocated display symbol so that it is written on to the soldier's retina at a location thereof that points toward the selected target.

34. A method for providing an enlarged view of an object to a user wearing the headgear according to claim 22, wherein when viewed without the headgear, the object is imaged over a narrow portion of the retina, the method comprising:
   (a) obtaining a digital image of the object; and
   (b) writing said image over an extended portion of the retina of the user so as to present an enlarged field of view.

35. A method for accurate navigation of a user wearing the headgear according to claim 22, without need of GPS in an open or confined space for which there is accessible a topographic map at high resolution, the method comprising:
   (a) identifying one or more distinctive landmarks in the distant scene selected by a user;
   (b) determining at least three distinctive features in total of the selected landmark or landmarks and identifying the distinctive features to the user by superimposing a guide mark on each of the distinctive features;
   (c) directing the user to set her line of sight on each of said distinctive features so that the line of sight is aligned with the guide marks;
   (d) measuring the user's direction of sight based on measured angular rotation of the 2-D scanning optics in the user's headgear;
   (e) correlating the precise location in space of each identified feature with a coordinate on the user's retina; and
   (f) computing the user's current location relative to the selected landmark and mapping the user's gaze with the open or confined space.

36. The method according to claim 35, further including:
   (g) identifying a remote location in the open or confined space to which the user requires directions;
   (h) determining from said topographic map a route from the user's current location to the remote location; and
   (i) providing directions to the user for reaching the remote location.

37. A method for alerting a motorist wearing the headgear according to claim 22, of involuntary departure from a predetermined direction of gaze, the method including:
   (a) monitoring the motorist's direction of gaze;
   (b) determining whether fluctuations in the direction of gaze are indicative of a potentially hazardous driving condition; and
   (c) if so, alerting the motorist.

38. A method for controlling an augmented reality (AR) application by a user wearing the headgear according to claim 22, the method comprising:
   (a) monitoring the user's direction of gaze for identifying an object in the AR application; and
   (b) following the user's direction of gaze for moving the object to a new location.

39. A method for remotely directing multiple mutually remote attendees at a teleconference when to speak, each remote attendee wearing headgear according to claim 22, and each having a respective unique identity and display symbol, the method comprising the following steps carried out by a conference organizer:
   (a) conveying images of each participant for projecting on to the retina of each participant so that each participant sees all participants at the same time; and (b) directing each participant when to speak either by writing an invitation to speak on to the retina of the invited participant; or by displaying on a screen seen by all attendees the respective unique symbol identifying the invited participant.

* * * * *